US009265858B2

(12) United States Patent
Larsen

(10) Patent No.: US 9,265,858 B2
(45) Date of Patent: Feb. 23, 2016

(54) DRY HAEMOSTATIC COMPOSITION

(71) Applicant: Ferrosan Medical Devices A/S, Søborg (DK)

(72) Inventor: Kristian Larsen, Værløse (DK)

(73) Assignee: Ferrosan Medical Devices A/S, Søborg (DK)

( * ) Notice: Subject to any disclaimer, the term of this patent is extended or adjusted under 35 U.S.C. 154(b) by 0 days.

(21) Appl. No.: 14/516,728

(22) Filed: Oct. 17, 2014

(65) Prior Publication Data
US 2015/0037314 A1 Feb. 5, 2015

Related U.S. Application Data

(63) Continuation of application No. PCT/DK2013/050191, filed on Jun. 12, 2013.

(60) Provisional application No. 61/658,586, filed on Jun. 12, 2012.

(30) Foreign Application Priority Data

Jun. 12, 2012 (DK) ................................ 2012 70319

(51) Int. Cl.
| | | |
|---|---|---|
| A61K 38/48 | (2006.01) |
| A61L 24/10 | (2006.01) |
| A61L 24/00 | (2006.01) |
| A61L 2/04 | (2006.01) |
| A61L 2/08 | (2006.01) |
| A61L 2/10 | (2006.01) |
| A61L 2/20 | (2006.01) |
| B65B 1/04 | (2006.01) |
| A61L 2/07 | (2006.01) |

(52) U.S. Cl.
CPC ................ *A61L 24/104* (2013.01); *A61L 2/04* (2013.01); *A61L 2/081* (2013.01); *A61L 2/082* (2013.01); *A61L 2/087* (2013.01); *A61L 2/10* (2013.01); *A61L 2/202* (2013.01); *A61L 2/204* (2013.01); *A61L 2/206* (2013.01); *A61L 2/208* (2013.01); *A61L 24/0015* (2013.01); *A61L 24/0036* (2013.01); *B65B 1/04* (2013.01); *A61L 2/07* (2013.01); *A61L 2300/254* (2013.01); *A61L 2300/802* (2013.01); *A61L 2400/04* (2013.01); *A61L 2400/06* (2013.01)

(58) Field of Classification Search
CPC ......... A61L 24/104; A61L 2/10; A61L 2/204; A61L 2/206; A61L 2/01; A61L 2/087; A61L 25/0015; A61L 2/208; A61L 2/081; A61L 2400/04; A61L 2300/254; A61L 2400/06; B65B 1/04
USPC ............... 424/94.64; 422/1; 53/469; 514/774
See application file for complete search history.

(56) References Cited

U.S. PATENT DOCUMENTS

| | | | |
|---|---|---|---|
| 2,465,357 A | 3/1949 | Correll et al. |
| 2,465,860 A | 3/1949 | Fleischmann |
| 2,507,244 A | 5/1950 | Correll |
| 2,558,395 A | 6/1951 | Studer |
| 2,899,362 A | 8/1959 | Sieger et al. |
| 3,089,815 A | 5/1963 | Kupelwieser et al. |
| 3,224,434 A | 12/1965 | Molomut et al. |
| 3,514,518 A | 5/1970 | Charier-Vadrot |
| 3,608,593 A | 9/1971 | McCormick et al. |
| 3,678,933 A | 7/1972 | Moore et al. |
| 3,815,580 A | 6/1974 | Oster |
| 3,869,539 A | 3/1975 | Kring et al. |
| 3,892,876 A | 7/1975 | Hobday et al. |
| 3,930,052 A | 12/1975 | De Brou et al. |
| 4,002,173 A | 1/1977 | Manning et al. |
| 4,006,220 A | 2/1977 | Gottlieb |
| 4,013,078 A | 3/1977 | Feild |
| 4,098,728 A | 7/1978 | Rosenblatt et al. |
| 4,107,288 A | 8/1978 | Oppenheim et al. |
| 4,124,705 A | 11/1978 | Rothman et al. |
| 4,150,744 A | 4/1979 | Fennimore |
| 4,164,559 A | 8/1979 | Miyata et al. |
| 4,179,400 A | 12/1979 | Tsao et al. |
| 4,194,392 A | 3/1980 | Lombard et al. |
| 4,208,439 A | 6/1980 | Hsu |
| 4,256,877 A | 3/1981 | Karlsson et al. |

(Continued)

FOREIGN PATENT DOCUMENTS

| | | |
|---|---|---|
| BG | 0051589 | 7/1993 |
| BG | 0099900 | 3/1997 |

(Continued)

OTHER PUBLICATIONS

"Formulation and Evaluation of Absorbable Gelatin Sponges," Chapter 3A of Rupali Kale thesis: *Design and Development of Surgical Dressings for Advanced Wound Management* (2010).
"Gelfoam Prescribing Information," Pharmacia & Upjohn (Nov. 1996).
"Gelfoam® Product Brochure," Pharmacia & Upjohn (Jun. 2013).
Smith, A., "New and Nonofficial Remedies: Absorbable Gelatin Sponge—Gelfoam-Upjohn," *Council on Pharmacy and Chemistry*, 135(14): p. 921 (1947).
Raftery, Andrew, "Absorbable haemostatic materials and intraperitoneal adhesion formation."; Br. J. Surg. 67; 1980; pp. 57-58.
Ansell, J., et al., "Gelfoam and Autologous Clot Embolization: Effect on Coagulation," *Investigative Radiology*, 13: 115-120 (1978).

(Continued)

*Primary Examiner* — Laura Schuberg
*Assistant Examiner* — Kara Johnson
(74) *Attorney, Agent, or Firm* — Hamilton, Brook, Smith & Reynolds, P.C.

(57) ABSTRACT

Disclosed is a dry composition, which upon addition of an aqueous medium forms a substantially homogenous paste suitable for use in haemostasis procedures. The paste forms spontaneously upon addition of the liquid, hence no mechanical mixing is required for said paste to form. Further disclosed are methods of preparing said dry composition, a paste made from said dry composition and use of said paste for medical and surgical purposes.

21 Claims, 2 Drawing Sheets

(56) References Cited

U.S. PATENT DOCUMENTS

| | | |
|---|---|---|
| 4,265,233 A | 5/1981 | Sugitachi et al. |
| 4,280,954 A | 7/1981 | Yannas et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,320,201 A | 3/1982 | Berg et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,416,813 A | 11/1983 | Ikeda et al. |
| 4,424,208 A | 1/1984 | Wallace et al. |
| 4,453,939 A | 6/1984 | Zimmerman |
| 4,482,386 A | 11/1984 | Wittwer et al. |
| 4,492,305 A | 1/1985 | Avery |
| 4,515,637 A | 5/1985 | Cioca |
| 4,522,302 A | 6/1985 | Paikoff |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,557,377 A | 12/1985 | Maloney |
| 4,559,304 A | 12/1985 | Kasai et al. |
| 4,600,574 A | 7/1986 | Lindner et al. |
| 4,640,834 A | 2/1987 | Eibl et al. |
| 4,655,211 A | 4/1987 | Sakamoto et al. |
| 4,685,597 A | 8/1987 | Hirao et al. |
| 4,696,812 A | 9/1987 | Silbering |
| 4,735,616 A | 4/1988 | Eibl et al. |
| 4,743,229 A | 5/1988 | Chu |
| 4,746,514 A | 5/1988 | Warne |
| 4,749,689 A | 6/1988 | Miyata et al. |
| 4,752,466 A | 6/1988 | Saferstein et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,851,521 A | 7/1989 | Della Valle et al. |
| 4,861,714 A | 8/1989 | Dean, Jr. et al. |
| 4,863,856 A | 9/1989 | Dean, Jr. et al. |
| 4,885,161 A | 12/1989 | Cornell |
| 4,891,359 A | 1/1990 | Saferstein et al. |
| 4,920,158 A | 4/1990 | Murray et al. |
| 4,925,677 A | 5/1990 | Feijen |
| 4,936,835 A | 6/1990 | Haaga et al. |
| 4,946,870 A | 8/1990 | Partain, III et al. |
| 4,965,203 A | 10/1990 | Silbering et al. |
| 4,982,769 A | 1/1991 | Fournier et al. |
| 4,997,753 A | 3/1991 | Dean, Jr. et al. |
| 5,007,916 A | 4/1991 | Linsky et al. |
| 5,017,229 A | 5/1991 | Burns et al. |
| 5,023,082 A | 6/1991 | Friedman et al. |
| 5,024,841 A | 6/1991 | Chu et al. |
| 5,037,740 A | 8/1991 | Tanaka et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,112,750 A | 5/1992 | Tanaka et al. |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro et al. |
| 5,162,430 A | 11/1992 | Rhee et al. |
| 5,165,938 A | 11/1992 | Knighton |
| 5,178,883 A | 1/1993 | Knighton |
| 5,180,583 A | 1/1993 | Hedner |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,281,528 A | 1/1994 | Boctor et al. |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,350,581 A | 9/1994 | Kochinke |
| 5,352,715 A | 10/1994 | Wallace et al. |
| 5,356,614 A | 10/1994 | Sharma |
| 5,356,883 A | 10/1994 | Kuo et al. |
| 5,384,333 A | 1/1995 | Davis et al. |
| 5,385,606 A | 1/1995 | Kowanko |
| 5,387,208 A | 2/1995 | Ashton et al. |
| 5,394,886 A | 3/1995 | Nabai et al. |
| 5,397,704 A | 3/1995 | Boctor et al. |
| 5,399,361 A | 3/1995 | Song et al. |
| 5,401,511 A | 3/1995 | Margalit |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Alleyne |
| 5,441,491 A | 8/1995 | Verschoor et al. |
| 5,443,481 A | 8/1995 | Lee |
| 5,447,966 A | 9/1995 | Hermes et al. |
| 5,456,693 A | 10/1995 | Conston et al. |
| 5,462,860 A | 10/1995 | Mach |
| 5,478,352 A | 12/1995 | Fowler |
| 5,503,848 A | 4/1996 | Perbellini et al. |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,599,735 A | 2/1997 | Moslehi |
| 5,614,587 A | 3/1997 | Rhee et al. |
| 5,618,551 A | 4/1997 | Tardy et al. |
| 5,643,596 A | 7/1997 | Pruss et al. |
| 5,645,849 A | 7/1997 | Pruss et al. |
| 5,648,506 A | 7/1997 | Desai et al. |
| 5,658,592 A | 8/1997 | Tanihara et al. |
| 5,660,854 A | 8/1997 | Haynes et al. |
| 5,667,839 A | 9/1997 | Berg |
| 5,669,934 A | 9/1997 | Sawyer |
| 5,672,336 A | 9/1997 | Sharma |
| 5,674,275 A | 10/1997 | Tang et al. |
| 5,690,675 A | 11/1997 | Sawyer et al. |
| 5,690,954 A | 11/1997 | Ilium |
| 5,698,213 A | 12/1997 | Jamiolkowski et al. |
| 5,700,476 A | 12/1997 | Rosenthal et al. |
| 5,712,161 A | 1/1998 | Koezuka et al. |
| 5,714,370 A | 2/1998 | Eibl et al. |
| 5,723,308 A | 3/1998 | Mach et al. |
| 5,743,312 A | 4/1998 | Pfeifer et al. |
| 5,749,895 A | 5/1998 | Sawyer et al. |
| 5,752,974 A | 5/1998 | Rhee et al. |
| 5,770,229 A | 6/1998 | Tanihara et al. |
| 5,791,352 A | 8/1998 | Reich et al. |
| 5,795,330 A | 8/1998 | Tofighi et al. |
| 5,798,091 A | 8/1998 | Trevino et al. |
| 5,804,203 A | 9/1998 | Hang et al. |
| 5,823,671 A | 10/1998 | Mitchell et al. |
| 5,824,015 A | 10/1998 | Sawyer |
| 5,853,749 A | 12/1998 | Hobbs |
| 5,856,356 A | 1/1999 | Tsouderos et al. |
| 5,861,043 A | 1/1999 | Carn |
| 5,863,496 A | 1/1999 | McElhany |
| 5,874,500 A | 2/1999 | Rhee et al. |
| 5,883,078 A | 3/1999 | Seelich et al. |
| 5,890,610 A | 4/1999 | Jansen et al. |

(56) References Cited

U.S. PATENT DOCUMENTS

| | | |
|---|---|---|
| 5,895,412 A | 4/1999 | Tucker |
| 5,902,832 A | 5/1999 | Van Bladel et al. |
| 5,908,054 A | 6/1999 | Safabash et al. |
| 5,931,165 A | 8/1999 | Reich et al. |
| 5,939,259 A | 8/1999 | Harvey et al. |
| 5,951,531 A | 9/1999 | Ferdman et al. |
| 5,951,583 A | 9/1999 | Jensen et al. |
| 5,957,166 A | 9/1999 | Safabash |
| 5,959,735 A | 9/1999 | Maris et al. |
| 5,986,168 A | 11/1999 | Noishiki et al. |
| 5,997,895 A | 12/1999 | Narotam et al. |
| 6,007,613 A | 12/1999 | Izoret |
| 6,027,741 A | 2/2000 | Cialdi et al. |
| 6,042,262 A | 3/2000 | Hajianpour |
| 6,045,570 A | 4/2000 | Epstein et al. |
| 6,056,970 A * | 5/2000 | Greenawalt et al. .......... 424/426 |
| 6,063,061 A | 5/2000 | Wallace et al. |
| 6,066,325 A | 5/2000 | Wallace et al. |
| 6,074,663 A | 6/2000 | Delmottet et al. |
| 6,096,309 A | 8/2000 | Prior et al. |
| 6,099,952 A | 8/2000 | Cercone |
| 6,110,484 A | 8/2000 | Sierra |
| 6,113,948 A | 9/2000 | Heath |
| 6,129,761 A | 10/2000 | Hubbell |
| 6,132,759 A | 10/2000 | Schacht et al. |
| 6,162,241 A | 12/2000 | Coury et al. |
| 6,166,130 A | 12/2000 | Rhee et al. |
| 6,168,788 B1 | 1/2001 | Wortham |
| 6,179,872 B1 | 1/2001 | Bell et al. |
| 6,218,176 B1 | 4/2001 | Berthold et al. |
| 6,261,596 B1 | 7/2001 | Li et al. |
| 6,277,394 B1 | 8/2001 | Sierra |
| 6,280,727 B1 | 8/2001 | Prior et al. |
| 6,283,933 B1 | 9/2001 | D'Aiessio et al. |
| 6,300,128 B1 | 10/2001 | Morota et al. |
| 6,303,323 B1 | 10/2001 | Laskey et al. |
| 6,312,474 B1 | 11/2001 | Francis et al. |
| 6,312,725 B1 | 11/2001 | Wallace et al. |
| 6,328,229 B1 | 12/2001 | Duronio et al. |
| 6,334,865 B1 | 1/2002 | Redmond et al. |
| 6,361,551 B1 | 3/2002 | Torgerson et al. |
| 6,364,519 B1 | 4/2002 | Hughes et al. |
| 6,387,413 B1 | 5/2002 | Miyata et al. |
| 6,416,739 B1 | 7/2002 | Rogerson |
| 6,454,787 B1 | 9/2002 | Maddalo et al. |
| 6,458,380 B1 | 10/2002 | Leaderman |
| 6,458,386 B1 | 10/2002 | Schacht et al. |
| 6,458,889 B1 | 10/2002 | Trollsas |
| 6,461,325 B1 | 10/2002 | Delmotte et al. |
| 6,472,162 B1 | 10/2002 | Coelho |
| 6,495,127 B1 | 12/2002 | Wallace et al. |
| 6,548,081 B2 | 4/2003 | Sadozai et al. |
| 6,584,858 B1 | 7/2003 | Miyazawa et al. |
| 6,620,436 B1 | 9/2003 | Rolf |
| 6,635,272 B2 | 10/2003 | Leaderman |
| 6,638,538 B1 | 10/2003 | Hashimoto et al. |
| 6,649,162 B1 | 11/2003 | Biering et al. |
| 6,706,690 B2 | 3/2004 | Reich et al. |
| 6,716,435 B1 | 4/2004 | Farmer et al. |
| 6,733,774 B2 | 5/2004 | Stimmeder |
| 6,831,058 B1 | 12/2004 | Ikada et al. |
| 6,887,974 B2 | 5/2005 | Pathak |
| 7,052,713 B2 | 5/2006 | Stimmeder |
| 7,056,722 B1 | 6/2006 | Coelho |
| 7,109,163 B2 | 9/2006 | Pendharkar et al. |
| 7,125,860 B1 | 10/2006 | Renier et al. |
| 7,320,962 B2 | 1/2008 | Reich et al. |
| 7,427,607 B2 | 9/2008 | Suzuki |
| 7,435,425 B2 | 10/2008 | Qian et al. |
| 7,547,446 B2 | 6/2009 | Qian et al. |
| 7,833,965 B2 | 11/2010 | Pendharkar et al. |
| 7,871,637 B2 | 1/2011 | Qian et al. |
| 7,923,431 B2 | 4/2011 | Wolff |
| 7,927,626 B2 | 4/2011 | Pendharkar et al. |
| 7,935,371 B2 | 5/2011 | Williams |
| 8,119,160 B2 | 2/2012 | Looney et al. |
| 8,303,981 B2 | 11/2012 | Wallace et al. |
| 8,357,378 B2 | 1/2013 | Wallace et al. |
| 8,512,729 B2 | 8/2013 | Wallace et al. |
| 8,551,941 B2 | 10/2013 | Pendharkar et al. |
| 8,603,511 B2 | 12/2013 | Wallace et al. |
| 8,642,831 B2 | 2/2014 | Larsen et al. |
| 2001/0008636 A1 | 7/2001 | Yamamoto et al. |
| 2001/0038848 A1 | 11/2001 | Donda |
| 2001/0041913 A1 | 11/2001 | Cragg et al. |
| 2002/0006429 A1 | 1/2002 | Redmond et al. |
| 2002/0010150 A1 | 1/2002 | Cortese et al. |
| 2002/0010482 A1 | 1/2002 | Watt et al. |
| 2002/0012982 A1 | 1/2002 | Blakesley et al. |
| 2002/0015724 A1 | 2/2002 | Yang et al. |
| 2002/0019062 A1 | 2/2002 | Lea et al. |
| 2002/0025921 A1 | 2/2002 | Petito et al. |
| 2002/0026215 A1 | 2/2002 | Redmond et al. |
| 2002/0027146 A1 | 3/2002 | de LaForcade et al. |
| 2002/0039594 A1 | 4/2002 | Unger |
| 2002/0042378 A1 | 4/2002 | Reich et al. |
| 2002/0061842 A1 | 5/2002 | Mansour et al. |
| 2002/0072767 A1 | 6/2002 | Zhu |
| 2002/0111576 A1 | 8/2002 | Greene et al. |
| 2002/0164322 A1 | 11/2002 | Schaufler |
| 2002/0173818 A1 | 11/2002 | Reever |
| 2002/0188196 A1 | 12/2002 | Burbank et al. |
| 2002/0192271 A1 | 12/2002 | Hedner et al. |
| 2002/0193448 A1 | 12/2002 | Wallace et al. |
| 2003/0004449 A1 | 1/2003 | Lafratta et al. |
| 2003/0008831 A1 | 1/2003 | Yang et al. |
| 2003/0009194 A1 | 1/2003 | Saker et al. |
| 2003/0012741 A1 | 1/2003 | Furlan et al. |
| 2003/0028140 A1 | 2/2003 | Greff |
| 2003/0032143 A1 | 2/2003 | Neff et al. |
| 2003/0064109 A1 | 4/2003 | Qian et al. |
| 2003/0095993 A1 | 5/2003 | Bentz et al. |
| 2003/0162708 A1 | 8/2003 | Wolfe et al. |
| 2003/0175410 A1 | 9/2003 | Campbell |
| 2003/0175419 A1 | 9/2003 | Sessa |
| 2003/0181659 A1 | 9/2003 | Naranda et al. |
| 2003/0232746 A1 | 12/2003 | Lamberti et al. |
| 2004/0076647 A1 | 4/2004 | Biering |
| 2004/0079763 A1 | 4/2004 | Powell |
| 2004/0101546 A1 | 5/2004 | Gorman et al. |
| 2004/0120993 A1 | 6/2004 | Zhang et al. |
| 2004/0197388 A1 | 10/2004 | Sceusa |
| 2004/0214770 A1 | 10/2004 | Reich et al. |
| 2004/0243043 A1 | 12/2004 | McCarthy et al. |
| 2004/0267352 A1 | 12/2004 | Davidson et al. |
| 2005/0008632 A1 | 1/2005 | Stimmeder |
| 2005/0031691 A1 | 2/2005 | McGurk et al. |
| 2005/0137512 A1 | 6/2005 | Campbell et al. |
| 2005/0171001 A1 | 8/2005 | Pendharkar et al. |
| 2005/0186253 A1 | 8/2005 | Lee et al. |
| 2005/0214277 A1 | 9/2005 | Schaufler |
| 2005/0218541 A1 | 10/2005 | Peng et al. |
| 2005/0245905 A1 | 11/2005 | Schmidt et al. |
| 2005/0284809 A1 | 12/2005 | Looney et al. |
| 2006/0002890 A1 | 1/2006 | Hersel et al. |
| 2006/0067976 A1 | 3/2006 | Ferraro et al. |
| 2006/0068013 A1 | 3/2006 | DiTizio et al. |
| 2006/0110381 A1 * | 5/2006 | Pendharkar .......... A61K 9/0019 424/94.64 |
| 2006/0115805 A1 | 6/2006 | Hansen |
| 2006/0121080 A1 | 6/2006 | Lye et al. |
| 2006/0121104 A1 | 6/2006 | Stern |
| 2006/0147492 A1 | 7/2006 | Hunter et al. |
| 2006/0159733 A1 | 7/2006 | Pendharkar et al. |
| 2006/0167561 A1 | 7/2006 | Odar et al. |
| 2006/0189516 A1 | 8/2006 | Yang et al. |
| 2006/0193846 A1 | 8/2006 | Stimmeder |
| 2006/0204490 A1 | 9/2006 | Pendharkar et al. |
| 2006/0255053 A1 | 11/2006 | Li |
| 2006/0282138 A1 | 12/2006 | Ota |
| 2007/0009578 A1 | 1/2007 | Moiler et al. |
| 2007/0025955 A1 | 2/2007 | Lowinger et al. |
| 2007/0086958 A1 | 4/2007 | Drake et al. |
| 2007/0128343 A1 | 6/2007 | Chappa |

(56) References Cited

U.S. PATENT DOCUMENTS

| | | |
|---|---|---|
| 2007/0160543 A1 | 7/2007 | Moiler |
| 2007/0250007 A1 | 10/2007 | Shekalim |
| 2007/0264130 A1 | 11/2007 | Mallett |
| 2007/0264301 A1 | 11/2007 | Cleek et al. |
| 2007/0264302 A1 | 11/2007 | Cleek et al. |
| 2008/0085316 A1 | 4/2008 | Qian et al. |
| 2008/0091277 A1 | 4/2008 | Deusch et al. |
| 2008/0095830 A1 | 4/2008 | Van Holten |
| 2008/0199539 A1 | 8/2008 | Baker et al. |
| 2008/0286376 A1 | 11/2008 | Qian et al. |
| 2008/0311172 A1 | 12/2008 | Schapira et al. |
| 2009/0087569 A1 | 4/2009 | Fan et al. |
| 2009/0142396 A1 | 6/2009 | Odar et al. |
| 2010/0028309 A1 | 2/2010 | Odar et al. |
| 2010/0048758 A1 | 2/2010 | Chen et al. |
| 2010/0063459 A1* | 3/2010 | Preiss-Bloom et al. ...... 604/265 |
| 2010/0143447 A1 | 6/2010 | Hansen |
| 2010/0292717 A1 | 11/2010 | Petter-Puchner et al. |
| 2010/0318048 A1 | 12/2010 | Hoeffinghoff et al. |
| 2011/0045034 A1 | 2/2011 | Nur et al. |
| 2011/0059228 A1 | 3/2011 | Gillick et al. |
| 2014/0220130 A1 | 8/2014 | Larsen et al. |
| 2015/0045830 A1 | 2/2015 | Jensen et al. |

FOREIGN PATENT DOCUMENTS

| | | |
|---|---|---|
| CN | 1270240 | 10/2000 |
| DE | 3146841 | 6/1983 |
| DE | 4119140 | 12/1992 |
| DE | 4407875 | 9/1995 |
| EP | 0132983 A1 | 2/1985 |
| EP | 0156649 | 10/1985 |
| EP | 0282316 | 9/1988 |
| EP | 0341007 | 11/1989 |
| EP | 0341745 | 11/1989 |
| EP | 0365705 | 5/1990 |
| EP | 0372966 | 6/1990 |
| EP | 0 385 916 | 9/1990 |
| EP | 0395758 | 11/1990 |
| EP | 0172710 | 3/1992 |
| EP | 0478827 | 4/1992 |
| EP | 0493387 | 10/1993 |
| EP | 0376931 | 6/1994 |
| EP | 0702081 | 3/1996 |
| EP | 0737467 | 10/1996 |
| EP | 0612252 | 5/1999 |
| EP | 0773740 | 11/1999 |
| EP | 1005874 | 6/2000 |
| EP | 1022031 | 7/2000 |
| EP | 1044693 | 10/2000 |
| EP | 1053758 | 11/2000 |
| EP | 1084720 | 3/2001 |
| EP | 1140235 | 10/2001 |
| EP | 1174463 | 1/2002 |
| EP | 1258256 | 11/2002 |
| EP | 1283063 | 2/2003 |
| EP | 0790823 | 7/2003 |
| EP | 0891193 | 8/2003 |
| EP | 1484070 | 12/2004 |
| EP | 1095064 | 6/2005 |
| EP | 1649867 | 4/2006 |
| EP | 1361906 | 4/2007 |
| EP | 1414370 | 4/2007 |
| EP | 1059957 | 8/2007 |
| EP | 1608230 | 7/2010 |
| FR | 2679772 | 5/1993 |
| FR | 2759980 | 8/1998 |
| GB | 697603 | 9/1949 |
| GB | 648619 | 1/1951 |
| GB | 1 037 937 | 8/1966 |
| GB | 1199887 | 7/1970 |
| GB | 1584080 | 2/1981 |
| GB | 1591654 | 6/1981 |
| GB | 2266239 | 10/1993 |
| GB | 2393120 | 3/2004 |
| GB | 2414021 | 11/2005 |
| JP | 51-125156 | 11/1976 |
| JP | 59-113889 | 6/1984 |
| JP | 60214728 | 10/1985 |
| JP | 62070318 | 3/1987 |
| JP | 62221357 | 9/1987 |
| JP | 01130519 | 5/1989 |
| JP | 05308969 | 11/1993 |
| JP | 06254148 | 9/1994 |
| JP | 08-024325 | 1/1996 |
| JP | 9-504719 | 5/1997 |
| JP | 10-507666 | 7/1998 |
| JP | 2002/513308 | 5/2002 |
| JP | 2004002271 | 1/2004 |
| JP | 2006-296896 | 11/2006 |
| JP | 07090241 | 4/2007 |
| JP | 2010228932 | 10/2010 |
| KR | 910007847 | 10/1991 |
| KR | 100751046 | 8/2007 |
| WO | WO 83/01244 | 4/1983 |
| WO | WO 86/00912 | 2/1986 |
| WO | WO 89/02730 | 4/1989 |
| WO | WO 90/13320 | 11/1990 |
| WO | WO 92/21354 | 12/1992 |
| WO | WO 92/22252 | 12/1992 |
| WO | WO 93/06802 | 4/1993 |
| WO | WO 93/06855 | 4/1993 |
| WO | WO 93/10768 | 6/1993 |
| WO | WO 93/21908 | 11/1993 |
| WO | WO 94/08552 | 4/1994 |
| WO | WO 94/17840 | 8/1994 |
| WO | WO 94/27630 | 12/1994 |
| WO | WO 95/12371 | 5/1995 |
| WO | WO 95/15747 | 6/1995 |
| WO | WO 95/25748 | 9/1995 |
| WO | WO 95/31955 | 11/1995 |
| WO | WO 96/04025 | 2/1996 |
| WO | WO 96/06883 | 3/1996 |
| WO | WO 96/07472 | 3/1996 |
| WO | WO 96/10374 | 4/1996 |
| WO | WO 96/10428 | 4/1996 |
| WO | WO 96/12447 | 5/1996 |
| WO | WO 96/14368 | 5/1996 |
| WO | WO 96/16643 | 6/1996 |
| WO | WO 96/39159 | 12/1996 |
| WO | WO 96/40033 | 12/1996 |
| WO | WO 97/17023 | 5/1997 |
| WO | WO 97/17024 | 5/1997 |
| WO | WO 97/17025 | 5/1997 |
| WO | WO 97/29792 | 8/1997 |
| WO | WO 97/37694 | 10/1997 |
| WO | WO 98/08550 | 3/1998 |
| WO | WO 98/31403 | 7/1998 |
| WO | WO 98/34546 | 8/1998 |
| WO | WO 98/36784 | 8/1998 |
| WO | WO 98/43092 | 10/1998 |
| WO | WO 98/44963 | 10/1998 |
| WO | WO 98/51282 | 11/1998 |
| WO | WO 99/04828 | 2/1999 |
| WO | WO 99/12032 | 3/1999 |
| WO | WO 99/13902 | 3/1999 |
| WO | WO 99/38606 | 8/1999 |
| WO | WO 99/44901 | 9/1999 |
| WO | WO 99/45938 | 9/1999 |
| WO | WO 99/51208 | 10/1999 |
| WO | WO 00/09018 | 2/2000 |
| WO | WO 00/18301 | 4/2000 |
| WO | WO 00/27327 | 5/2000 |
| WO | WO 00/61201 | 10/2000 |
| WO | WO 00/74742 | 12/2000 |
| WO | WO 00/76533 | 12/2000 |
| WO | WO 01/13956 | 3/2001 |
| WO | WO 01/28603 | 4/2001 |
| WO | WO 01/34206 | 5/2001 |
| WO | WO 01/54735 | 8/2001 |
| WO | WO 01/66161 | 9/2001 |
| WO | WO 01/97826 | 12/2001 |
| WO | WO 02/18450 | 3/2002 |

(56) References Cited

FOREIGN PATENT DOCUMENTS

| | | |
|---|---|---|
| WO | WO 02/22059 | 3/2002 |
| WO | WO 02/22184 | 3/2002 |
| WO | WO 02/40068 | 5/2002 |
| WO | WO 02/058749 | 8/2002 |
| WO | WO 02/064182 | 8/2002 |
| WO | WO 02/070594 | 9/2002 |
| WO | WO 03/004072 | 1/2003 |
| WO | WO 03/007845 | 1/2003 |
| WO | WO 03/024426 | 3/2003 |
| WO | WO 03/024429 | 3/2003 |
| WO | WO 03/055531 | 7/2003 |
| WO | WO 03/070110 | 8/2003 |
| WO | WO 03/094983 | 11/2003 |
| WO | WO 2004/028404 | 4/2004 |
| WO | WO 2004/028423 | 4/2004 |
| WO | WO 2004/028583 | 4/2004 |
| WO | WO 2004/029095 | 4/2004 |
| WO | WO 2004/030711 | 4/2004 |
| WO | WO 2004/035629 | 4/2004 |
| WO | WO 2004/053051 | 6/2004 |
| WO | WO 2004/075650 | 9/2004 |
| WO | WO 2004/084869 | 10/2004 |
| WO | WO 2004/108035 | 12/2004 |
| WO | WO 2004/108179 | 12/2004 |
| WO | WO 2004/108418 A1 | 12/2004 |
| WO | WO 2005/000265 | 1/2005 |
| WO | WO 2005/009225 | 2/2005 |
| WO | WO 2005/041811 | 5/2005 |
| WO | WO 2005/044285 | 5/2005 |
| WO | WO 2005/062889 | 7/2005 |
| WO | WO 2005/063217 A1 | 7/2005 |
| WO | WO 2005/072700 | 8/2005 |
| WO | WO 2005/084650 A1 | 9/2005 |
| WO | WO 2005/107713 | 11/2005 |
| WO | WO 2006/005340 | 1/2006 |
| WO | WO 2006/031358 | 3/2006 |
| WO | WO 2006/034568 | 4/2006 |
| WO | WO 2006/063758 | 6/2006 |
| WO | WO 2006/128471 | 12/2006 |
| WO | WO 2007/001926 | 1/2007 |
| WO | WO 2007/018887 A2 | 2/2007 |
| WO | WO 2007/092618 | 8/2007 |
| WO | WO 2007/133699 | 11/2007 |
| WO | WO 2007/137839 | 12/2007 |
| WO | WO 2008/016983 | 2/2008 |
| WO | WO 2008/051758 | 5/2008 |
| WO | WO 2008/090555 | 7/2008 |
| WO | WO 2009/020612 A1 | 2/2009 |
| WO | WO 2009/109194 | 9/2009 |
| WO | WO 2009/109963 | 9/2009 |
| WO | WO 2009/131752 A2 | 10/2009 |
| WO | WO 2011/151384 | 12/2011 |
| WO | WO 2011/151386 | 12/2011 |
| WO | WO 2011/151400 | 12/2011 |
| WO | WO 2012/146655 | 11/2012 |
| WO | WO 2013/053753 | 4/2013 |
| WO | WO 2013/053755 | 4/2013 |
| WO | WO 2013/053759 | 4/2013 |
| WO | WO 2013/060770 | 5/2013 |
| WO | WO 2013/131520 a2 | 9/2013 |
| WO | WO 2014/086996 | 6/2014 |

OTHER PUBLICATIONS

Barton, B., et al., "Fibrin Glue as a Biologic Vascular Patch—A Comparative Study," *Journal of Surgical Research*, vol. 40, 1 page; abstract retrieved from http://www.ncbi.nlm.nih.gov on Jan. 3, 2001. (1986).

Baxter, "GentaFleece Collagen Fleece—Version 5: Instructions for Use—Collagen Sponge with Antibiotic Protection for Surgical Use," Retrieved from http://www.advancingbiosurgery.com/en_EU/downloads/ifu_gentafleece.pdf on Mar. 2002, 2 pages. English portion second column of first page.

Baxter, "Product Catalogue: Collagen," 4 pages, retrieved from http://www.baxter-ecommerce.com/ecatalog on Feb. 2, 2006 (2006).

Baxter, "TissuFleece E Package Leaflet," *Baxter International Inc.*, 4 pages, English portion of instructions for use (2003).

Baxter, "TissuFleece E, TissuCone E and TissuFoil E: Biomaterials," *Basic scientific Information*, 9 pages (2003).

Boland, T., et al., "Application of Inkjet Printing to Tissue Engineering," *Biotechnol. J.*, 1: 910-917 (2006).

Boyers, S., et al., "Reduction of Postoperative Pelvic Adhesions in the Rabbit with Gore-Tex Surgical Membrane Fertility and Sterility," vol. 49, No. 6, pp. 1066-1070 (1988).

Brannon-Peppas, L., et al., "The Equilibrium Swelling Behavior of Porous and Non-Porous Hydrogels," *Absorbent Polymer Technology*, Elsevier, Amsterdam, pp. 67-102 (1990).

Branski et al., "Mucosal Wound Healing in a Rabbit Model of Subglottic Stenosis"; Arch Otolaryngol Head Neck Surg, vol. 131, Feb. 2005, p. 153-157.

Campbell, P.G., et al., "Engineered Spatial Patterns of FGF-2 Immobilized on Fibrin Direct Cell Organization," *Biomaterials*, 26: 6762-6770 (2005).

Campbell, P.G., et al., "Tissue Engineering with the Aid of Inkjet Printers," *Expert Opin. Biol. Ther.*, 7: 1123-1127 (2007).

Canal, T., et al., "Correlation Between Mesh Size and Equilibrium Degree of Swelling of Polymeric Networks" *Biomedical Materials Research*, 23: 1183-1193 (1989).

Cantor et al., "Gelfoam® and Thrombin in treatment of massive gastroduodenal hemorrhage—A preliminary report". *American Journal of Surgery*, Dec. 1950.

Cantor, M., et al., "Gelfoam and Thrombin in Gastroduodenal Bleeding: An Experimental Study," *Journal of Laboratory and Clinical Medicine*, 35(6): 890-893 (1950).

Cantor, M., et al., "Gelfoam and Thrombin in Treatment of Massive Upper Gastrointestinal Hemorrhage," *American Journal of Surgery*, 82(2): 230-05 (1951).

Changez et al., Abstract of "Efficacy of antibiotics-loaded interpenetrating network (IPNs) hydrogel based on poly (acrylic acid) and gelatin for treatment of experimental osteomyelitis: in vivo study.", Biomaterials; 26(14): 2095-2104 (2005).

Chaplin, J.M., et al., "Use of an Acellular Dermal Allograft for Dural Replacement: An Experimental Study," *Neurosurgery*, 45(2): 320-327 (1999).

Cheung, D., et al., "Mechanism of Crosslinking of Proteins by Glutaraldehyde IV: In Vitro and In Vivo Stability of a Crosslinked Collagen Matrix," *Connective Tissue Research*, 25: 27-34 (1990).

Christensen, F, et al., "Qualitative Description of the Wurster-Based Fluid- Bed Coating Process," *Drug Dev and Industry Pharmacy*, 23(5): 451-463 (1977).

Chuang, V., et al., "Sheath Needle for Liver Biopsy in High-Risk Patients Radiology,", 166: 261-262 (1988).

Coenye, et al., "A Qualitative Morphological comparison of Two Heamostatic Agents in a Porcine Liver Trauma Model," *Surgical Science*, 4: 359-364 (2013).

Collins, D., et al., "Enemata of Gelfoam Milk Suspension Combined with Thrombin-Solution to Control Massive Hemorrhage Following Anorectal Surgery," *The American Journal of Proctology*, 2: 60-63 (1951).

Collins, R., et al., "Use of Collagen Film as a Dural Substitute: Preliminary Animal Studies," *Journal of Biomedical Materials Research*, 25: 267-276 (1991).

De la Torre, et al., "Hemostasis and Hemostatic agents in minimally invasive surgery", *Surgery*, 142(4S): S39-S45 (2007).

De Iaco et al., "Efficacy of a Hyaluronan Derivative gel in postsurgical adhesion prevention in the presence of inadequate hemostasis." *Surgery*, 130(1): 60-64 (2001).

DeLustro, F., et al., "A Comparative Study of the Biologic and Immunologic Response to Medical Devices Derived From Dermal Collagen," *Journal of Biomedical Materials Research*, 20: 109-120 (1986).

Dembo M.A. et al.; Abstract of "Antiseptic hemostatic preparations, their properties and study.", Lech.Prep. Krovi. Tkanei; 1974; pp. 139-140.

Dodd et al., "Minimally invasive treatment of malignant hepatic tumors. At the threshold of a major breakthrough", *Radiographies* 20: 9-27 (2000).

(56) References Cited

OTHER PUBLICATIONS

Drognitz et al., Abstract of "Release of vancomycin and teicoplanin from a plasticized and resorbable gelatin sponge: in vitro investigation of a new antibiotic delivery system with glycopeptides."; *Indection Germany* (Minich); 34(1): 29-34 (2006).

Duchene, D., et al., "Pharmaceutical and Medical Aspects of Bioadhesive Systems for Drug Administration," *Drug Dev and Industr Pharmacy*, 14(2&3):283-318 (1988).

Edgerton, M., et al., "Vascular Hamatomas and Hemagiomas: Classification and Treatment," *Southern Medical Journal*, 75(12): 1541-1547 (1982).

Ellegala et al., "Use of FloSeal Hemostatic Sealant in Trans-sphenoidal Pituitary Surgery: Technical Note."; *Neurosurgery*, 51: 513-516 (Aug. 2002).

Filippi, R., et al., "Bovine Pericardium for Duraplasty: Clinical Results in 32 Patients," *Neurological Review*, 20:103-107 (2001).

Flory, P., "Phase Equilibria in Polymer Systems," *Principles of Polymer Chemistry*, 13: 541-594 (1953).

Fujii, et al., "Safety of GT XIII (report 2)—Japanese+English translation," *The Clinical Report*, vol. 20, No. 17 (Dec. 1986).

Gall, R.M., "Control of Bleeding in Endoscopic Sinus Surgery: Use of a Novel Gelatin-Based Hemostatic Agent",*Journal of Otolaryngology*, 31(5): (2002).

Gibble, et al., "Fibrin glue: the perfect operative sealant?" *Reviews: Transfusion*, 30(8): 741-747 (1990).

Guinto, F., "Preparation of Gelfoam Particles Using an Orthopedic Rasp," *Radiology*, 153: 250 (1984).

Gurny, R., et al., "Bioadhesive Intraoral Release Systems: Design, Testing and Analysis," *Biomaterials*, 5: 336-340 (1984).

Harris, W.H., et al., "Topical Hemostatic Agents for Bone Bleeding in Humans," *The Journal of Bone and Joint Surgery*, 60-A(4): 454-456 (1978).

Heller, J., et al., "Release of Norethindrone from Poly(Ortho Esters)," *Polymer Engineering and Science*, 21: 727-731 (1981).

Herndon, J., et al., "Compression of the Brain and Spinal Cord Following Use of Gelfoam," *Arch. Surg*, 104: 107 (Jan. 1972).

Hieb, L., et al, "Spontaneous Postoperative Cerebrospinal Fluid Leaks Following Application of Anti-Adhesion Barrier Gel," *SPINE*, 26(7): 748-751 (2001).

Hill et al., "Use of microfibrillar collagen hemostat (avitenet) and thrombin to achieve hemostats after median sternotomy."; *J. Thorac Cardiovasc Surg.*, 108: 1151-1152 (1994).

Hill-West et al., "Efficacy of a resorbable hydrogel barrier, oxidized regenerated cellulose and hyaluronic acid in the prevention of ovarian adhesions in a rabbit model."; *Fertility and Sterility*, 62(3): 630-634 (1994).

Hong et al., Abstract of "Study on gelatin-containing artificial skin IV: a comparative study on the effect of antibiotic and EGF on cell proliferation during epidermal healing."; *Biomaterials* 22(20): 2777-2783 (2001).

Hong, et al., "The Use of Hemostatic Agents and Sealants in Urology", *The Journal of Urology*, 176: 2367-2374 (2006).

Hood, D., et al., "Efficacy of Topical Hemostat Floseal Matrix in Vascular Surgery," *24th World Congress of the International Society for Cardiovascular Surgery*, Sep. 12-16, 1999, 2 pages.

International Preliminary Report on Patentability and Written Opinion of the International Searching Authority for International Application No. PCT/DK2011/050082, "A Method for Promotion of Hemostasis and/or Wound Healing," dated Jul. 6, 2012.

International Preliminary Report on Patentability, PCT/DK2007/050196, "Wound or Tissue Dressing Comprising Lactic Acid Bacteria", May 29, 2009.

International Search Report & Written Opinion of the International Searching Authority, PCT/DK2007/050196, "Wound or Tissue Dressing Comprising Lactic Acid Bacteria", Apr. 23, 2008.

International Search Report from counterpart International Application No. PCT/DK2011/050082, "A Method for Promotion of Hemostasis and/or Wound Healing," dated Jun. 21, 2011.

International Search Report for International Application No. : PCT/DK2013/050191, "Dry Haemostatic Composition", date of mailing: Aug. 21, 2013.

Jeong, B., et al., "Biodegradable Block Copolymers as Injectable Drug-Delivery Systems," *Nature*, 388: 860-862 (1997).

Jonas, R., et al., "A new sealant for knitted Dacron prostheses: Minimally cross-linked gelatin," *Journal of Vascular Surgery*, 7(3): 414-419 (1988).

Katayama, et al., "GT XIII safety ($3^{rd}$ report)—Japanese+English translation," *The Clinical Report*, vol. 20 (1986).

Kelly M.J. et al., "The value of an operative wound swab sent in transport medium in the prediction of later clinical wound infection: A controlled clinical and bacteriological evaluation.", *Brit. J. Surgery*, 65: 81-88 (1978).

Kim, K., et al., "Reduction in Leg Pain and Lower-Extremity Weakness with Oxiplex/SP Gel for 1 Year after Laminevtomy, Laminotomy, and Disectomy," *Neurosurgical Focus*, 17: 1-6 (2004).

Kline, D., et al., "Dural Replacement with Resorbable Collagen," *Archives of Surgery*, 91: 924-929 (1965).

Knopp, U., "A New Collagen Foil Versus a Cadaveric Dura Graft for Dural Defects—A Comparative Animal Experimental Study," *European Association of Neurosurgical Societies—Proceedings of the $12^{th}$ European Congress of Neurosurgery*, Lisbon, 2003, 17 pages.

Kocak et al., "Reduction of adhesion formation with cross-linked hyaluronic acid after peritoneal surgery in rats.", Fertility and Sterility 72(5): 873-878 (1999).

Kofidis, T., et al., "Clinically Established Hemostatis Scaffold (Tissue Fleece) as Biomatrix in Tissue and Organ Engineering Research," *Tissue Engineering*, 9: 517-523 (2003).

Krill, D., et al., "Topical Thrombin and Powdered Gelfoam: An Efficient Hemostatic Treatment for Surgery," *Journal of Tennessee Dental Association*, 66(2): 26-27 (1986).

Kuhn, J., et al., "Bilateral Subdural Heamatomata and Lumbar Pseudomeningocele Due to a Chronic Leakage of Liquor Cerebrospinalis after a Lumbar Disectomy with the Application of ADCON-L Gel," *Journal of Neurology, Neurosergery & Psychiatry*, 76: 1031-1033 (2005).

Langer, R., et al., "Chemical and Physical Structure of Polymers as Carriers for Controlled Release of Bioactive Agents: A Review," *Journal of Macromolecular Science—Reviews in Macromolecular Chemistry and Physics*, C23: 61-126 (1983).

Laquerriere, A., et al., "Experimental Evaluation of Bilayered Human Collagen as a Dural Substitute," *Journal of Neurosurgery*, 78: 487-491 (1993).

Larson, P., "Topical Hemostatic Agents for Dermatologic Surgery," *Journal of Dermatologic Surgery & Oncology*, 14: 623-632 (1988).

Larsson et al., "Surgicel®—an absorbable hemostatic material—in prevention of peritoneal adhesion in rats."; *Acta Chir Scand.*, 26(144): 375-378 (1978).

Laurent et al., "Hyaluronic acid reduces connective tissue formation in middle ears filled with absorbable gelatin sponge: An experimental study.", *Am J.Otolaryngol*, 7: 181-186 (1986).

Le, A., et al., "Unrecognized Durotomy After Lumbar Discectomy: A Report of Four Cases Associated with the Use of ADCON-L," *Spine*, 26(1): 115-118 (2001).

Lee, P., "Interpretation of Drug-Release Kinetics from Hydrogel Matrices in Terms of Time-Dependent Diffusion Coefficients," *Controlled-Release Technology—Pharmaceutical Applications*, Ch. 5, ACS Symposium Series 348, pp. 71-83 (1986).

Leong, K., et al., "Polyanhydrides for Controlled Release of Bioactive Agents," *Biomaterials*, 7: 364-371 (1986).

Leong, K., et al., "Polymeric Controlled Drug Delivery," *Advanced Drug Delivery Reviews*, 1: 199-233 (1987).

Lewis, Kevin, et al., "Comparison of Two Gelatin and Thrombin Combination Hemostats in a Porcine Liver Abrasion Model," *Journal of Investigative Surgery*, vol. 26: 141-148 (2013).

Li et al., "Evaluation of esterified hyaluronic acid as middle ear-packing material.", *Arch Otolaryngol Head Neck Surg*, 127: 534-539 (2001).

Loeb, J, "The Influence of Electrolytes Upon the Osmotic Pressure of Gelatin Solutions", *J. Biol. Chem.*, 35: 497-508 (1918).

(56) References Cited

OTHER PUBLICATIONS

Luengo et al., "Prevention of peritoneal adhesions by the combined use of Spongostan and 32% Dextran 70: An experimental study in pigs." *Fertility and Sterility*, 29(4): 447-450 (1978).

M.G. Cascone et al., "Collagen and hyaluronic acid based polymeric blends as drug delivery systems for the release of physiological concentrations of growth hormone." *Journal of Materials science: Materials in Medicine*; 5: 770-774 (1994).

Masar, E., et al., "Synthesis of Polyurethanes and Investigation of their Hydrolytic Stability," *Journal of Polymer Science: Polymer Symposium*, 66: 259-268 (1979).

Masuzawa, M., et al., "Experimental Study Related to the Hemostasis Action of GT XIII," *The Clinical Report*, 20(2): 471-476 (Feb. 1986).

Matsumoto, K., et al., "A Gelatin Coated Collagen-Polyglycolic Acid Composite Membrane as a Dural Substitute," *American Society for Artificial Internal Organs Journal*, 47: 641-645 (2001).

Maxson et al., "Efficacy of a modified oxidized cellulose fabric in the prevention of adhesion formation." *Gynecol. Obstet. Invest.*, 26: 160-165 (1988).

McClure, J., et al., "Massive Gastroduodenal Hemorrhage: Treatment with Powdered Gelfoam and Buffered Thrombin Solution," *Surgery*, 32: 630-637 (1952).

McPherson, J., et al., "An Examination of the Biologic Response to Injectable, Glutaraldehyde Cross-linked Collagen Implants," *Journal of Biomedical Materials Research*, 20: 93-107 (1986).

McPherson, J., et al., "Development and Biochemical Characterization of Injectable Collagen," *J. Dermatol. Surg. Oncol.*, 12(1): 13-20 (Jul. 7, 1988).

McPherson, J., et al., "The Effects of Heparin on the Physiochemical Properties of Reconstituted Collagen," *Collagen and Related Research*, 1: 65-82 (1988).

McPherson, J., et al., "The Preparation and Physiochemical Characterization of an Injectable Form of Reconstituted, Glutaraldehyde Crosslinked, Bovine Corium Collagen," *Journal of Biomedical Materials Research*, 20: 79-92 (1986).

Meddings, N., et al., "Collagen Vicryl—A New Dural Prosthesis," *Acta Neurochirurgica*, 117: 53-58 (1992).

Mello, L., et al., "Duraplasty with Biosynthetic Cellulose: An Experimental Study," *Journal of Neurosurgery*, 86: 143-150 (1997).

Miller, D., and Peppas, N., "Diffusional Effects During Albumin Adsorption on Highly Swollen Poly(vinyl Alcohol) Hydrogels," *Eur. Polym. J.*, 24(7): 611-615 (1988).

Miller, E.D., et al., "Dose-Dependent Cell Growth in Response to Concentration Modulated Patterns of FGF-2 Printed on Fibrin," *Biomaterials*, 27: 2213-2221 (2006).

Millikan, L., "Treatment of Depressed Cutaneous Scars with Gelatin Matrix Implant: A Multicenter Study," *J. Am. Acad. Dermatol.*, 16: 1155-1162 (1987).

Moak, E., "Hemostatic Agents: Adjuncts to Control Bleeding," *Today's O.R. Nurse*, pp. 6-10 (1991).

Mueller, K., "Release and Delayed Release of Water-Soluble Drugs from Polymer Beads with Low Water Swelling," *Controlled-Release Technology—Pharmaceutical Applications*, Ch. 11, ACS Symposium Series 348: 139-157 (1986).

Narotam, P., et al., "A Clinicopathological Study of Collagen Sponge as a Dural Graft in Neurosurgery," *Journal of Neurosurgery*, 82: 406-412 (1995).

Narotam, P., et al., "Experimental Evaluation of Collagen Sponge as a Dural Graft," *British Journal of Neurosurgery*, 7: 635-641 (1993).

Nimni, M., et al., "Chemically Modified Collagen: A Natural Biomaterial for Tissue Replacement," *Journal of Biomedical Materials Research*, 21: 741-771 (1987).

Nimni, M., Ph.D., "The Cross-Linking and Structure Modification of the Collagen Matrix in the Design of Cardiovascular Prosthesis," *Journal of Cardiac Surgery*, 3: 523-533 (1988).

Nogueira et al., Comparison of gelatine matrix-thrombin sealants used during laparoscopic partial nephrectomy, *BJU International*, 102: 1670-1674 (2008).

Novak, D., "Embolization Materials," *Interventional Radiology*, pp. 295-313 (1990).

O'Neill, P., et al., "Use of Porcine Dermis as a Dural Substitute in 72 Patients," *Journal of Neurosurgery*, 61: 351-354 (1984).

Ofner and Bubnis, "Chemical and Swelling Evaluations of Amino Group Crosslinking in Gelatin and Modified Gelatin Matrices," *Pharma. Res.*, 13: 1821-1827 (1996).

Oz et al., "Controlled clinical trial of a novel hemostatic agent in cardiac surgery.", *Ann Thorac Surg.* 2000; vol. 69; 2000; pp. 1376-1382.

Oz, et al., "Floseal-Matrix: New Generation Topical Hemostatic Sealant", *J. Card. Surg.*, 18: 486-493 (2003).

Parizek, J., et al., "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery," *Acta Neurochirurgica*, 139: 827-838 (1997).

Park, Y-K., et al., "Prevention of Arachnoiditis and Postoperative Tethering of the Spinal Cord with Gore-Tex Surgical Membrane: An Experimental Study with Rats," *Neurosurgery*, 42(4): 813-824 (1998).

Peppas, N. and Barr-Howell, B., "Characterization of the Cross-Linked Structure of Hydrogels," *Ch. 2: Hydrogels in Medicine and Pharmacy, vol. I: Fundamentals*, N. Peppas ed., pp. 27-56 (1986).

Peppas, N. and Brannon-Peppas, L, "Hydrogels at Critical Conditions. Part 1. Thermodynamics and Swelling Behavior," *Journal of Membrane Science*, 48: 281-290 (1990).

Peppas, N. and Kharc, A., "Preparation, Structure and diffusional Behavior of Hydrogels in Controlled Release," *Adv. Drug Delivery Reviews*, 11: 1-35 (1993).

Peppas, N. and Korsmeyer, R, "Dynamically Swelling Hydrogels in Controlled Release Applications," *Ch. 6: Hydrogels in Medicine and Pharmacy, vol. III: Properties and Applications*, N. Peppas ed., pp. 109-135 (1987).

Peppas, N. and Lustig, S., "Solute Diffusion in Hydrophilic Network Structures," *Ch. 3: Hydrogels in Medicine and Pharmacy, vol. I: Fundamentals*, N. Peppas ed., pp. 57-83 (1986).

Peppas, N. and Mikos, A., "Preparation Methods and Structure of Hydrogels," Ch. 1: *Hydrogels in Medicine and Pharmacy, vol. I: Fundamentals*, N. Peppas ed., pp. 1-25 (1986).

Peppas, N. and Moynihan, H, "Structure and Physical Properties of Poly(2-Hydroxyethyl Methacrylate) Hydrogels," *Ch. 2: Hydrogels in Medicine and Pharmacy, vol. II: Polymers*, N. Peppas ed., pp. 49-64 (1987).

Peppas, N., "Hydrogels and Drug Delivery," *Current Opinion in Colloid & Interface Science*, 2: 531-537 (1997).

Peppas, N., "Hydrogels in Medicine and Pharmacy," *Hydrogels in Medicine and Pharmacy*, vol. 1. Fundamentals, CRC Press, Boca Raton, FL, 180 pages. (1986).

Peppas, N., "Hydrogels in Medicine and Pharmacy," *Hydrogels in Medicine and Pharmacy*, vol. 2. Polymers, CRC Press, Boca Raton, FL, 172 pages. (1987).

Peppas, N., "Hydrogels in Medicine and Pharmacy," *Hydrogels in Medicine and Pharmacy*, vol. 3. Properties and Applications, CRC Press, Boca Raton, FL, 196 pages. (1987).

Peppas, N., "Hydrogels of Poly (Vinyl Alcohol) and its Copolymers," *Ch. 1. Hydrogels in Medicine and Pharmacy, vol. II: Polymers*, N. Peppas ed., pp. 57 pgs (1987).

Peppas, N., ed., "Other Biomedical Applications of Hydrogels," *Ch. 9: Hydrogels in Medicine and Pharmacy, vol. III: Properties and Applications*, pp. 177-186 (1987).

Pietrucha, K., "New Collagen Implant as Dural Substitute," *Biomaterials*, 12: 320-323 (1991).

Porchet, F., et al., "Inhibition of Epidural Fibrosis with ADCON-L: Effect on Clinical Outcome One Year Following Reoperation for Recurrent Lumbar Radiculopathy," *Neurological Research*, 21: 551-560 (1999).

Product leaflet for FloSeal® Matrix Hemostatic Sealant dated Jul. 2001.

Purdy et al., "Microfibrillar collagen model of canine cerebral infarction"; *Strokes*, 20(10): 1361-1367 (Oct. 1989).

(56) References Cited

OTHER PUBLICATIONS

Quintavalla et al., "Fiuorescently labeled mesenchymal stem cells (MSCs) maintain mutlilineage potential and can be detected following implantation into Particular cartilage defects.", *Biomaterials* 23: 109-119 (2002).
Raul, J.S., et al., "Utilisation du Polyester Urethane (NEUROPATCH) Comme Substitut Dural," *Neurochirugie*, 49: 83-89, English abstract only on p. 83 (2003).
Reddy, M., et al., "A Clinical Study of a Fibrinogen-Based Collagen Fleece for Dural repair in Neurosergery," *Acta Neurochirurgica*, 144: 265-269 (2002).
Reese, "Role of fibronectin in wound healing", Report date: Sep. 12, 1986; Annual rept. Oct. 1, 1985-Mar. 31, 1986, Final rept. Oct. 1, 1983-Mar. 31, 1986. Corporate Author: Medical Coli of Gerogia Augusta Research Institute. Brunt and Klausner, "Growth factors speed wound healing", Nature Biotechnology 6(1): 25-30 (1988).
Reijnen et al., "Prevention of intra-abdominal abscesses and adhesions using a hyaluronic acid solution in a rat peritonitis model." *Arch Surg.* 134: 997-1001 (1999).
Renkens, K., et al, "A Multicenter, Prospective, Randomized Trial Evaluating a New Hemostatic Agent for Spinal Surgery," *Spine*, 26(15): 1645-1650 (2001).
Riley, S., et al. "Percutaneous Liver Biopsy with Plugging of Needle Track: A Safe Method for Use in Patients with Impaired Coagulation," *Lancet*, p. 436 (1984).
Roda, et al., "Protein Microdeposition Using a Conventional Ink-Jet Printer," *BioTechniques*, 28(3): 492-496 (2000).
Rosenblatt, J., et al., "Effect of Electrostatic Forces on the Dynamic Rheological Properties of Injectable Collagen Biomaterials," *Biomaterials*, 13: 878-886 (1982).
Rosenblatt, J., et al., "Injectable Collagen as a pHSensitive Hydrogel," *Biomaterials*, 12: 985-995 (1984).
Ross, J., et al., "Association Between Peridural Scar and Recurrent Radicular Pain After Lumbar Discectomy: Magnetic Resonance Evaluation," *Neurosurgery*, pp. 855-863 (1996).
Rossler, B., et al., "Collagen Microparticles: Preparation and Properties," *Journal of Microencapsulation*, 12: 49-57 (1995).
Sakurabayashi et al., "Clinical evaluation of new hemostatic agent for hemostasis from biopsy wounds in the liver."; Gastroenterological Endoscopy 30:(10) 29 pgs. (Oct. 1988).
Sanfilippo et al., "Comparison of avitene, topical thrombin and Gelfoam as sole hemostatic agent in tuboplasties.", Fertility and Sterility 33(3): 311-316 (1980).
San-Galli, F., et al., "Experimental Evaluation of a Collagen-Coated Vicryl Mesh as a Dural Substitute," *Neurosurgery*, 30: 396-401 (1992).
Santomaso et al., "Powder flowability and density rations: the impact of granules packing", *Chemical Engineering Science* 58: 2857-2874 (2003).
Schramm, V., et al., "Gelfoam Paste Injection for Vocal Cord Paralysis," *The Laryngoscope*, 88: 1268-73 (1978).
Shaffrey, C.I., et al., "Neurosurgical Applications of Fibrin Glue: Augmentation of Dural Closure in 134 Patients," *Neurosurgery*, 26: 207-210 (1990).
Shushan et al., "Hyaluronic acid for preventing experimental postoperative intraperitoneal adhesions.", *Journal of Reproductive Medicine*, 39(5): 398-402 (1994).
Shuxian, M. and Zhili, C., "Clinical Observation of the Treatment of Hemoptysis by Ultrasonic Atomizing Inhalation of Thrombin", *Chinese Journal of Critical Care Medicine*, 16(2): 30 (1996).
Sidman, K., et al., "Biodegradable, Implantable Sustained Release Systems Based on Glutamic Acid Copolymers," *Journal of Membrane Science*, 7: 227-291 (1979).
Simamora, P., et al., "Controlled delivery of pilocarpine. 2. In-vivo evaluation of Gelfoam® device," *International Journal of Pharmaceutics*, 170(2): 209-214 (1998).
Smith, K., et al., "Delayed Postoperative Tethering of the Cervical Spinal Cord," *Journal of Neurosurgery*, 81: 196-201 (1994).
Soules et al., "The prevention of postoperative pelvic adhesions: An animal study comparing barrier methods with Dextran 70.", *Am. J. Obstet. Gynecol.*, 143(7): 829-834 (1982).
Spence et al., "Cerebellar capillary hemangioblastoma: its histogenesis studied by organ culture and electron microscopy.", *Cancer*, 35(2): 326-341 (Feb. 1975).
Springorum, H., "Die Verwendung von Kollagenfolien Zur Uberbruckung von Defekten des Gleitgewebes bei Achillotenotomien und Achillessehnenrupturen," *Akt. Traumatol.*, 15: 120-121, English abstract only on p. 120 (1985).
Stricker, A., et al., "Die Verwendung von TissuFoil Membran bei der Sinusbodenaugmentation," *Ellipse*, 17: 1-5 (2001). English abstract only on p. 1.
Sugitachi, A., et al., "A Newly Devised Chemo-Embolic Agent, G.T. XIIIADM," *Gan. To. Kagaku Ryoho*, 12: 1942-1943 (1985). English abstract retrieved from http://www.ncbi.nlm.nih.gov/ on Jan. 2, 2001.
Sugitachi, A., et al., "Locoregional Therapy in Patients with Malignant Pleural Effusion—Two Different Kinds of 'BAC Therapy'," *Gan. To. Kagaku Ryoho*, 19: 1640-1643 (1992). English abstract retrieved from http://www.ncbi.nlm.nih.gov on Jan. 3, 2001.
Sugitachi, A., et al., "Preoperative Transcatheter Arterial Chemo-Embolization for Locally Advanced Breast Cancer: Application for New Thrombotic Materials." *Japanese Journal of Surgery*, 13: 456-458 (1992).
Surgiflo® product leaflet, "Surgiflo® Hemostatic Matrix Kit," 5 pages (2012).
Swann, "Studies on hyaluronic acid—I. The preparation and properties of rooster comb hyaluronic acid", *Biochemica et biophysica acta*, 156: 17-30 (1968).
Taheri, Z., "The Use of Gelfoam Paste in Anterior Cervical Fusion," *Journal of Neurosurgery*, 34: 438 (1971).
Tobin, M., et al., "Plugged Liver Biopsy in Patients with Impaired Coagulation," *Digestive Diseases and Science*, 34: 13-15 (1989).
Tucker, H., "Absorbable Gelatin (Gelfoam) Sponge," Springfield, Illinois, Charles T. Thomas, pp. 3-125 (1965).
Van den Bosch, et al., "Gelatin degradation at elevated temperature", *International Journal of Biological Macromolecules*, 32: 129-138 (2003).
Vandelli, M.A., et al., "The effect of the crosslinking time period upon the drug release and the dynamic swelling of gelatin microspheres," *Pharmazie*, 46: 866-869 (1991).
Vander salm T.J. et al., Abstract of "Reduction of sternal infection by application of topical vancomycin.", J. of Thoracic and Cardiovascular Surgery; 98(4): 618-622 (1989).
Vinas, F., et al., "Evaluation of Expanded Polytetrafluoroethylene (ePTFE) versus Polydioxanone (PDS) for the Repair of Dura Mater Defects," *Neurological Research*, 21: 262-268 (1999).
Wachoi-Drewek et al., "Comparative investigation of drug delivery of collagen implants saturated in antibiotic solutions and a sponge containing gentamicin.", Biomaterials, 17: 1733-1738 (1996).
Wallace, D., "The Relative Contribution of Electrostatic Interactions to Stabilization of Collagen Fibrils," *Biopolymers*, 29: 1015-1026 (1990).
Wallace, D., et al., "Injectable Cross-Linked Collagen with Improved Flow Properties," *Journal of Biomedical Materials Research*, 23: 931-945 (1989).
Warren, W., et al., "Dural Repair Using Acellular Human Dermis: Experience with 200 Cases: Technique Assessment," *Neurosurgery*, 46: 1391-1396 (2000).
Wassersug, J.D., M.D., "Use of Human Thrombin in Some Cases of Pulmonary Hemorrhage" *Pulmonary Hemorrhage*, vol. XVII, pp. 354-356 (Mar. 1950).
West et al., "Efficacy of adhesion barriers: Resorbable hydrogel, oxidized regenerated cellulose and hyaluronic acid.", *The Journal of Reproductive Medicine*, 41(3) 149-154 (1996).
Wiesenthal et al., Abstract of "New method for packing the external auditory canal, middle ear space, and mastoid cavities after otologic surgery.", *The Journal of Otolaryngology*; 28(5): 260-265 (1999).
Wilkinson, H., et al., "Gelfoam Paste in Experimental Laminectomy and Cranial Trephination," *Journal of Neurosurgery*, 54: 664-667 (1981).

(56) References Cited

OTHER PUBLICATIONS

Written Opinion of the International Preliminary Examining Authority for International Application No. PCT/DK2011/050082, "A Method for Promotion of Hemostasis and/or Wound Healing," dated Mar. 23, 2012.
Xing, Q., et al., "Increasing Mechanical Strength of Gelatin Hydrogels by Divalent Metal Ion Removal", Sci. Rep., 4: 4706: DOI:10.1038/srep04706(2014).
Xu et al., "Viability and electrophysiology of neural cell structures generated by the inkjet printing method", Biomaterials, 27: 3580-3588 (2006).
Xu, T., et al., "Inkjet Printing of Viable Mammalian Cells," Biomaterials, 26: 93-99 (2005).
Y.S. Choi et al., "Studies on Gelatin-Based Sponges. Part III: A Comparative Study of Cross-linked Gelatin/ Alginate, Gelatin/ Hyaluronate and Chitosan/Hyaluronate Sponges and their Application as a wound dressing in fullthickness skin defect of rat.", J. of Mat. Sci.; Mat. In Med.; 12: 67-73 (Jan. 2001).
Choi, Y.S. et al., "Studies on gelatin-containing artificial skin: II. Preparation and characterization of cross-linked gelatin-hyaluronate sponge.", J. Biomed Mater Res., 48: 631-639 (1999).
Yaping, G., "Observation and Nursing of the Treatment of Hemoptysis of Pulmonary Tuberculosis by Ultrasonic Atomizing Inhalation of Thrombin", Journal of Qilu Nursing, 10(2): 126 (Feb. 2004).
Youwen, W. et al., "Clinical Observation of the Therapeutic Efficacy of the Treatment of 15 Patients with Hemoptysis by Ultrasonic Atomizing Inhalation of Thrombin", Chengdu Medical Journal, 30(5): 262 (Oct. 2004).
Yuesong et al., Abstract of "Design and experimental study of a slow-release antibiotic membrane implant in surgery wound.", Intern. Des Services de San. Des Forces Armees; 72(7-9): 194-196 (Sep. 1999).
Yuki, N., et al., "Effects of Endoscopic Variceal Sclerotherapy Using GT XIII on Blood Coagulation Tests and the Renal Kallikrein-Kinin System," Gastroentral. Japan, 25: 561-567 (1990). English abstract retrieved from http://www.ncbi.nlm.nih.gov Jan. 2, 2001.
Ziegelaar, B., et al., "The Characterisation of Human Respiratory Epithelial Cells Cultured on Resorbable Scaffords: First Steps Towards a Tissue Engineered Tracheal Replacement," Biomaterials, 23: 1425-1438 (2002).
Ziegelaar, B., et al., "Tissue Engineering of a Tracheal Equivalent, Doctoral Thesis," Munich, Germany, Ludwig Maximilians University, 2004, 25 pages (2004).
Zins, M., et al., "US-Guided Percutaneous Liver Biopsy with Plugging of the Needle Track: A Prospective Study in 72 High-Risk Patients," Radiology, 184: 841-843 (1992).
International Preliminary Report for International Application No. PCT/DK2003/000855 "Gelatine-Based Materials as Swabs" Date of Completion: Jun. 2, 2005.
International Preliminary Report on Patentability (Corrected Version) for International Application No. PCT/DK2005/000063, "Haemostatic Sprays and Compositions", completed Nov. 6, 2006.
International Preliminary Report on Patentability for International Application No. PCT/DK2005/000475, "Haemostatic Composition Comprising Hyaluronic Acid", completed Aug. 16, 2006.
International Preliminary Report on Patentability for International Application No. PCT/DK2009/050048, "Device for Promotion of Hemostasis and/or Wound Healing", completed Sep. 6, 2010.
International Preliminary Report on Patentability for International Application No. PCT/DK2011/050082, "A Method for Promotion of Hemostasis and/or Wound Healing", mailed Jul. 6, 2012.
Notification of the International Search Report and Written Opinion of the International Searching Authority from counterpart International Application No. PCT/DK2011/050082, "A Method for Promotion of Hemostasis and/or Wound Healing", mailed Jun. 21, 2011.
International Search Report for International Application No. PCT/DK2005/000475, "Haemostatic Composition Comprising Hyaluronic Acid", mailed Oct. 25, 2005.
International Search Report for International Application No. PCT/DK2009/050048, "Device for Promotion of Hemostasis and/or Wound Healing", Date of mailing: Apr. 6, 2010.
International Search Report for International Application No. PCT/DK2013/050054 "Pressurized Container Containing Haemostatic Paste" Date of Mailing: Sep. 9, 2013.
International Search Report for International Application No. PCT/DK2003/000855 "Gelatine-Based Materials as Swabs" Date of Mailing: Oct. 8, 2004.
Surgiflo Hemostatic Matrix (Made from SURGIFOAM Absorbable Gelatin Sponge U S P.) plus FlexTip (2 pages) (2008).
Surgiflo Haemostatic Flex Tip, Johnson & Johnson Wound Management (84 pages) (Mar. 2007).
Surgiflo Hemostatic Matrix—Essential Prescribing Information Package Insert (2005).
Surgiflo Hemostatic Matrix, Johnson & Johnson Wound Management, a division of Ethicon, Inc. (12 pages) (2005).
Written Opinion of the International Searching Authority (Corrected Version) for International Application No. PCT/DK2005/000063, "Haemostatic Sprays and Compositions", received Jul. 26, 2005.
Written Opinion of the International Searching Authority for International Application No. PCT/DK2005/000475, "Haemostatic Composition Comprising Hyaluronic Acid", received Oct. 24, 2005.
Written Opinion of the International Searching Authority for International Application No. PCT/DK2009/050048, "Device for Promotion of Hemostasis and/or Wound Healing", Date of completion: Aug. 31, 2010.
English Derwent Abstract of Ranjane reference, Nov. 18, 1997.
FloSeal Matrix Hemosealant, Instructions of Use, Retrieved from Internet URL http://www.etsnet.org/file/vendors/931/pdf/140.pdf [retrieved on Aug. 17, 2005].
Gelfoam absorbable powder. Retrieved from Internet URL: http://www.fda.gov/cdrh/pdf/N18286S012c.pdf [retrieved on May 22, 2009].
International Search Report for International Application No. PCT/DK2005/000063, "Haemostatic Sprays and Compositions", received Jul. 28, 2005.
International Search Report for International Application No. PCT/DK2009/050048, "Device for Promotion of Hemostasis and/or Wound Healing", mailed on Apr. 6, 2010.
Raftery, A., "Absorbable haemostatic materials and intraperitoneal adhesion formation."; Br. J. Surg. 67; 1980; pp. 57-58.
Solar Biologicals Inc., "Solar-cult sampling products: Pre-moistened cellulose sponge sampling systems", available at www.solarbiologicals.com/samp-sys.htm (Jul. 25, 2002).
Written Opinion of the International Searching Authority for International Application No. PCT/DK2009/050048, "Device for Promotion of Hemostatis and/or Wound Healing", completed Aug. 31, 2010.
Wu, Y. et al., Abstract of "Design and experimental study of a slow-release antibiotic membrane implant in surgery wound.", Intern. Des Services de San. Des Forces Armees; 72(7-9): 194-196 (Sep. 1999).
Fiss, I., et al., "Use of Gelatin-Thrombin Hemostatic Sealant in Cranial Neurosurgery," Neurologia Medico-Chirurgica, 47(10):462-467 (2007).
Mitsuhashi, J., "Invertabrate Tissue Culture Methods," Springer Lab Manual, p. 407 (2002).
Oyelese, Yinka, et al., "Postpartum Hemhorrage," Obstetrics and Gynecology Clinics of North America 34.3, 421-441 (2007).
Pschyrembel®—Klinisches Wörterbuch, 261st edition, de Gruyter (2007).
Sigma-Aldrich Datasheet for "Hank's Balanced Salts," revised Apr. 2007.
Spotnitz, W. D., et al., "Hemostatus, Sealants, and Adhesives: Components of the Surgical Toolbox," Transfusion, 48(7):1502-1516 (2008).
Stief, T. W., "Kallikrein Activates Prothrombin," Clinical and Applied Thrombosis/Hemostasis, 14.1:97-98 (2008).
Final Office Action for U.S. Appl. No. 14/136,578, titled: "Device for Promotion of Hemostasis and/or Wound Healing", dated Feb. 26, 2015 "Dry Haemostatic Composition".

(56) References Cited

OTHER PUBLICATIONS

Non-Final Office Action for U.S. Appl. No. 14/136,578, titled: "Device for Promotion of Hemostasis and/or Wound Healing", dated: Oct. 2, 2014.
Stuart Transport medium information sheet [retrieved online on May 27, 2009] www.Condalab.com, Dehydrated Culture Media.
Weeks, R., "Microscopy of Soft Materials," *Chapter 1 in Experimental and Computational Techniques in Soft Condensed Matter Physics*, Jeffrey Olafsen, Ed, 2010.
26th Annual Symposium: Clinical Update in Anaesthesiology, Surgery and Perioperative Medicine, Jan. 20-25, 2008.
Arai, K., et al., "Clinical Effect of Thrombin-Collagen Sponge Sheet in Surgical Field," Chiryo (Pharmacology and Treatment), 11(5):413-418 (1983). (English translation of Office Action for Japanese counterpart application 2010-547957, Title: Device for Promotion of Hemostasis and/or Wound Healing, being provided to satisfy concise explanation requirement under 37 C.F.R. 1.98(a)(3)).
Barrow, D.L., et al., "The Use of Greater Omentum Vascularized Free Flaps for Neurosurgical Disorders Requiring Reconstruction", *Journal of Neurosurgery*, 60: 305-311 (1984).—Best available copy.
Hae-Won et al., Abstract of "Porus scaffolds of gelatin-hydroxyapatite nanocomposites obtained by biometic approach: Characterization and antibiotic drug release."; J. of Biomedical Materials Research 74B(2); 2005; pp. 686-698.
Hotz, G., et al., "Collagen and Fibrin as Biologic Binders from Granular Hydroxyapatite," Deutsche Zeitschrift fur Mund-Kieferund Gesichts-Chirurgie, 13(4): 296-300 (1989). Abstract retrieved from http://www.ncbi.nlm.nih.gov on Jan. 3, 2001.
Kost J., and Langer R., "Equilibrium Swollen Hydrogels in Controlled Release Applications," Ch. 5: Hydrogels in Medicine and Pharmacy, vol. III: properties and Applications, N. Peppas ed., pp. 95-108 (1987).
Lee, J., et al., "Experimental Evaluation of Silicone-Coated Dacron and Collagen Fabric-Film Laminate as Dural Substitutes," Journal of Neurosurgery, 27: 558-564 (1967). Best available copy.
Maurer, P, et al., "Vicryl (Polyglactin 910) Mesh as a Dural Substitute," Journal of Neurosurgery, 63:448-452 (1985).
Min et al., "Molecular Weight Changes of Sodium Hyaluronate Powder and Solution by Heat treatment," Matrix Biology Institute, Proceedings of Hyaluronan, Oct. 11-16, 2003.
Palm, S., et al., "Dural Closure with Nonpenetrating Clips Prevents Meningoneural Adhesions: An Experimental Study in Dogs," Neurosurgery, 45(4): 875-882 (1999).
Pitt, C., et al., "Biodegradable Drug Delivery Systems Based on Aliphatic Polyesters: Application to Contraceptives and Narcotic Antagonists," Controlled Release of Bioactive Materials, R. Baker, Ed., New York, Academic Press, pp. 19-43 (1980).
Ratner, B., "Hydrogel Surfaces," Ch. 4: Hydrogels in Medicine and Pharmacy, vol. I: Fundamentals, N. Peppas ed., pp. 85-94 (1986).
Verhoeven, A.G., et al., "XV. The use of microporous polymeric powders for controlled release drug delivery systems," Controlled Drug Delivery. Ch. 15, International Symposium of the Association for Pharmaceutical Technology (APV), Bad Homburg, Nov. 12-14, 1984, pp. 226-237.
Written Opinion of the International Searching Authority for International Application No. PCT/DK2007/050196, "Wound or Tissue Dressing Comprising Lactic Acid Bacteria", date of mailing: Apr. 23, 2008.

* cited by examiner

DRY HAEMOSTATIC COMPOSITION

RELATED APPLICATIONS

This application is a continuing application of International Application No. PCT/DK2013/050191, which designated the United States and was filed on Jun. 12, 2013, published in English, which claims priority under 35 U.S.C. §119 or 365 to Denmark Application No. PA 2012 70319, filed Jun. 12, 2012 and U.S. Provisional Application No. 61/658,586, filed Jun. 12, 2012. The entire teachings of the above applications are incorporated herein by reference.

FIELD OF INVENTION

The present invention relates to a dry composition suitable for use in haemostasis and/or wound healing, wherein the dry composition forms a paste spontaneously upon addition of an aqueous medium and methods of preparing said dry composition. The invention further relates to use of said composition.

BACKGROUND OF INVENTION

Protein-based haemostatic materials such as collagen and gelatine are commercially available in solid sponge and loose or unpacked powder form for use in surgical procedures. Mixing of the loose or unpacked powder with a fluid such as saline or thrombin may form a paste or slurry that is useful as a haemostatic composition for use in cases of diffuse bleeding, particularly from uneven surfaces or hard to reach areas, depending on mixing conditions and relative ratios of the materials.

Conventional haemostatic pastes are prepared at the point of use by mechanical agitation and mixing of loose powder and liquid to provide uniformity of the composition. Mixing of the powder and fluid may be conducted in a container, such as a beaker. Such mixing requires transfer of the powder from its original container to the beaker, addition of the fluid to the beaker containing the powder, and then kneading of the mixture to form the paste. Only after the paste is thus formed may the paste be placed into a delivery means or applicator, e.g. a syringe, and applied to the wound.

WO 03/055531 relates to a container comprising a fixed amount of haemostatic agent in powder form, such as gelatine powder. Upon addition of a suitable amount of liquid, mechanical mixing within the container is performed by closing the lid and shaking the container. The resultant putty-like haemostatic paste can then be removed from the container and applied to a patient to promote haemostasis.

Alternately, attempts have been made to preload one syringe (Syringe I) with loose gelatine powder, and a second syringe (Syringe II) with liquid. When it is time to make a paste, Syringes I and II are connected via a luer lock and the solution in Syringe II is pushed into Syringe I. By attempting to pass the solution and powder repeatedly back and forth between Syringes I and II, a homogeneous paste may or may not be formed. Often in a surgical situation, a haemostatic paste with optimal powder:liquid ratio cannot be obtained due to insufficient mixing of the powder and the liquid in a syringe. Even if such methods of mixing are successful in forming a paste, the time and mechanical effort required to form the paste are undesirable or even unacceptable. Also the mixing can affect the final density of the paste (too intense mixing may result in a lower density paste) and hence inconsistent consistency of the paste from time to time.

Floseal Haemostatic Matrix (Baxter) is a kit for producing a haemostatic gelatine paste. The gelatine paste is produced by first making a thrombin solution and then transferring the gelatin matrix-thrombin solution mixture back and forth between two connected syringes for a total of at least twenty passes. The paste can then be applied to a patient to promote haemostasis directly from the syringe.

Likewise, Surgiflo® Haemostatic Matrix (Ethicon) is a kit for producing a haemostatic gelatine paste comprising thrombin, which is prepared by transferring the gelatin matrix-thrombin solution mixture back and forth between two connected syringes for a total of at least 6 passes.

US 2005/0284809 relates to a method for preparing a haemostatic paste that more readily absorbs aqueous liquids, such that less mechanical force and time is required in order to form a flowable haemostatic paste. The paste of US 2005/0284809 is prepared from compressed haemostatic powder particles and to prepare the paste, it must be transferred back and forth between connected syringes for a total of at least 5 passes.

WO 2011/151400 relates to a process for making a dry haemostatic composition comprising a coagulation inducing agent such as thrombin and a biocompatible polymer such as gelatine. The coagulation inducing agent and the biocompatible polymer are mixed to form a paste and the paste is subjected to lyophilisation. The resulting dry composition is reconstituted by transferring the composition and a diluent back and forth between two connected syringes for a total of at least twenty passes as described previously.

Such mixing procedures and manipulations are time consuming and may potentially compromise the sterility of the haemostatic paste. It would be desirable if a haemostatic composition could be provided which would eliminate the need for such undesirable mixing requirements.

SUMMARY OF INVENTION

The present invention relates to a dry composition, which upon addition of an adequate amount of an aqueous medium forms a substantially homogenous paste suitable for use in haemostasis procedures. The paste forms spontaneously upon addition of the liquid, i.e. no mechanical mixing is required for said paste to form.

The invention further relates to a method of preparing said dry composition comprising the steps of:
  a. providing a biocompatible polymer in powder form, one or more polyols and an aqueous medium,
  b. mixing the biocompatible polymer, the one or more polyols and the aqueous medium to obtain a paste, and
  c. drying the paste.

The biocompatible polymer is preferably suitable for use in haemostasis and/or wound healing.

Uses of the paste formed from the dry composition are likewise covered by the present invention.

DEFINITIONS

Figure 1:
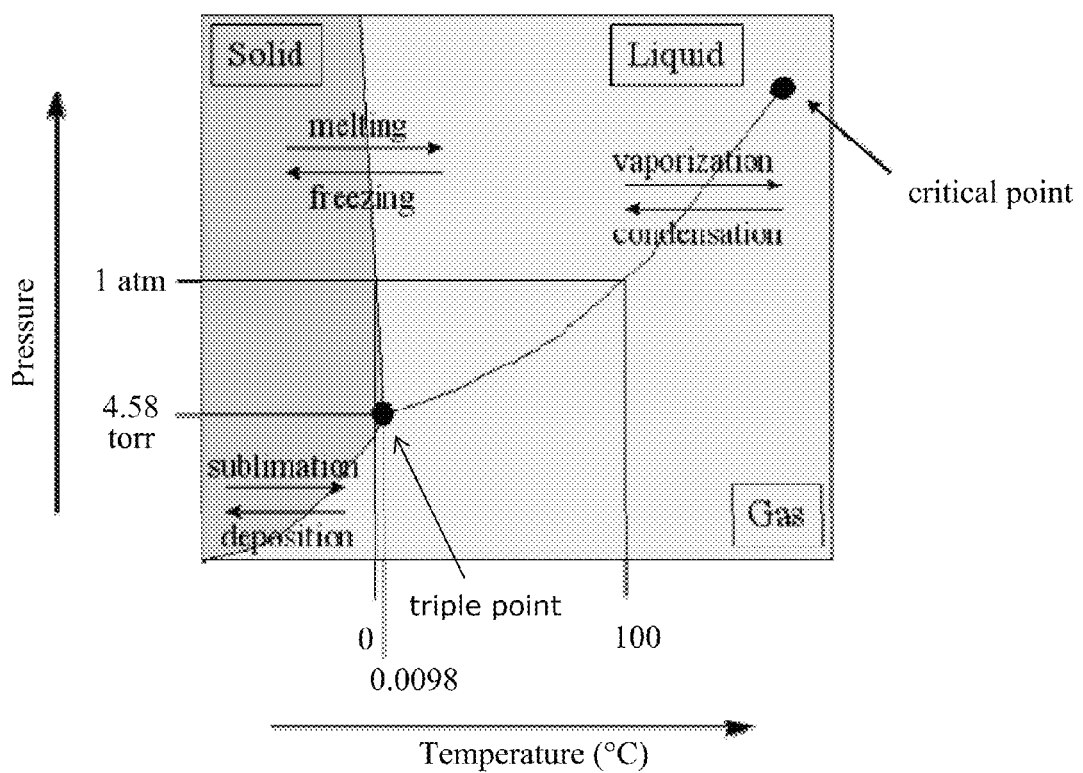
FIG. 1. Phase diagram of water. The phase diagram shows, in pressure-temperature space, the lines of equilibrium or phase boundaries between the three phases of solid, liquid, and gas.

A "bioactive agent" is any agent, drug, compound, composition of matter or mixture which provides some pharmacologic, often beneficial, effect that can be demonstrated in vivo or in vitro. An agent is thus considered bioactive if it has interaction with or effect on a cell tissue in the human or animal body. As used herein, this term further includes any physiologically or pharmacologically active substance that produces a localized or systemic effect in an individual. Bioactive agents may be a protein, such as an enzyme. Further examples of bioactive agents include, but are not limited to, agents comprising or consisting of an oligosaccharide, a polysaccharide, an optionally glycosylated peptide, an optionally glycosylated polypeptide, an oligonucleotide, a polynucleotide, a lipid, a fatty acid, a fatty acid ester and secondary metabolites. It may be used either prophylactically, therapeutically, in connection with treatment of an individual, such as a human or any other animal.

"Biocompatible" refers to a material's ability to perform its intended function without eliciting any undesirable local or systemic effects in the host.

"Biologically absorbable" is a term which in the present context is used to describe that the materials of which the said powder are made can be degraded in the body to smaller molecules having a size which allows them to be transported into the blood stream. By said degradation and absorption the said powder materials will gradually be removed from the site of application. For example, gelatine can be degraded by proteolytic tissue enzymes to absorbable smaller molecules, whereby the gelatine when applied in tissues typically is absorbed within about 4-6 weeks and when applied on bleeding surfaces and mucous membranes typically within 3-5 days.

A "gel" is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack). In this way gels are a dispersion of molecules of a liquid within a solid in which the solid is the continuous phase and the liquid is the discontinuous phase. A gel is not a paste or slurry.

"Haemostasis" is a process which causes bleeding to diminish or stop. Haemostasis occurs when blood is present outside of the body or blood vessels and is the instinctive response for the body to stop bleeding and loss of blood. During haemostasis three steps occur in a rapid sequence. Vascular spasm is the first response as the blood vessels constrict to allow less blood to be lost. In the second step, platelet plug formation, platelets stick together to form a temporary seal to cover the break in the vessel wall. The third and last step is called coagulation or blood clotting. Coagulation reinforces the platelet plug with fibrin threads that act as a "molecular glue".

A "haemostatic agent" according to the present invention is a biologically absorbable material. Examples of suitable biologically absorbable materials include but are not limited to gelatine, collagen, chitin, chitosan, alginate, cellulose, polyglycolic acid, polyacetic acid and mixtures thereof.

"International Unit (IU)". In pharmacology, the International Unit is a unit of measurement for the amount of a substance, based on biological activity or effect. It is abbreviated as IU, UI, or as IE. It is used to quantify vitamins, hormones, some medications, vaccines, blood products, and similar biologically active substances.

A "paste" according to the present invention has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes paste to demonstrate properties of fragile matter. A paste is not a gel/jelly. A "slurry" is a fluid mixture of a powdered/pulverized solid with a liquid (usually water). Slurries behave in some ways like thick fluids, flowing under gravity and being capable of being pumped if not too thick. A slurry may be regarded as a thin paste, i.e. a slurry generally contains more water than a paste.

"Percentage". If nothing else in indicated, the percentage is w/w.

"Spontaneous". The term "spontaneous" is used to describe phenomena arising from internal forces or causes, which are independent of external agencies or stimuli and which happen within a short period of time, i.e. preferably within less than about 30 seconds, more preferred within less than about 20 seconds, even more preferred within less than about 10 seconds or within less than about 5 seconds.

DETAILED DESCRIPTION OF THE INVENTION

The present invention relates to a dry composition, which upon addition of an adequate amount of an aqueous medium forms a substantially homogenous paste suitable for use in haemostasis procedures. The paste forms spontaneously upon addition of the liquid component, i.e. no mechanical mixing is required for said paste to form.

The dry composition may be prepared by a method comprising the sequential steps of:
 a. providing a biocompatible polymer in powder form, one or more polyols and an aqueous medium,
 b. mixing the biocompatible polymer, the one or more polyols and the aqueous medium to obtain a paste, and
 c. drying the paste.

The present invention further relates to a paste suitable for use in haemostasis and/or wound healing procedures prepared by adding an aqueous medium to the dry composition and use of said paste for promoting haemostasis and/or wound healing.

The advantages of the present invention are numerous and include:
 Less time spent preparing the paste, e.g. bleeding can be stopped faster.
 Decreased risk of compromising the sterility of the paste during preparation due to less handling steps.
 Decreased risk of making mistakes during preparation due to the simplified preparation of the paste.
 Optimal consistency of paste obtained every time.
 Bioactive agents, which are unstable in solution may be added to the paste prior to drying and will thus be present in the dry composition of the invention. For example, thrombin may be added to the paste prior to drying, thereby avoiding the time-consuming and error-prone thrombin dilution steps.

All of the above factors lead to increased patient safety.

Biocompatible Polymer

The present invention relates to a biocompatible agent in powder form, which is used to create a paste. The paste is then dried to obtain a dry composition suitable for use in haemostasis and wound healing procedures.

The biocompatible polymer of the present invention may be a biologic or a non-biologic polymer. Suitable biologic polymers include proteins, such as gelatin, soluble collagen, albumin, hemoglobin, casein, fibrinogen, fibrin, fibronectin, elastin, keratin, and laminin; or derivatives or combinations thereof. Particularly preferred is the use of gelatin or soluble non-fibrillar collagen, more preferably gelatin. Other suitable biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible.

The paste of the present invention may either comprise a single biocompatible polymer or a mixture of two or more biocompatible polymers.

In one embodiment, the biocompatible polymer is biologically absorbable. Examples of suitable biologically absorbable materials include gelatine, collagen, chitin, chitosan, alginate, cellulose, oxidised cellulose, polyglycolic acid, polyacetic acid and combinations thereof. It will be understood that various forms thereof, such as linear or cross-linked forms, salts, esters and the like are also contemplated for the present invention.

In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

In a preferred embodiment the polymer is cross-linked.

Any suitable cross-linking methods known to a person of skill may be used including both chemical and physical cross-linking methods.

In one embodiment of the present invention the polymer has been cross-linked by physical means, such as by dry heat. The dry heat treatment is usually performed at temperatures between 100° C. and 250° C., such as about 110° C. to about 200° C. In particular the temperature may be in the range of 110-160° C., e.g. in the range of 110-140° C., or in the range of 120-180° C., or in the range of 130-170° C., or in the range of 130-160° C., or in the range of 120-150° C. The period of time for cross-linking may be optimised by a skilled person and is normally a period between about 10 minutes to about 12 hours, such as about 1 hour to about 10 hours, for example between about 2 hours to about 10 hours, such as between about 4 hours to about 8 hours, for example between about 5 hours to about 7 hours, such as about 6 hours.

Examples of suitable chemical cross-linking agents include but are not limited to aldehydes, in particular glutaraldehyde and formaldehyde, acyl azïde, caboiimides, hexamethylene diisocyanate, polyether oxide, 1,4-butanediol-diglycidyl ether, tannic acid, aldose sugars, e.g. D-fructose, genipin and dye-mediated photo-oxidation. Specific compounds include but are not limited to 1-(3-dimethylaminopropyl)-3-ethylcarboiimide hydrochloride (EDC), dithiobis (propanoic dihydrazide) (DTP), 1-ethyl-3-(3-dimethylaminopropyl)-carbodiimide (EDAC).

The biocompatible polymer may be obtained from cross-linked sponges of gelatine or collagen, in particular cross-linked sponges of gelatine (such as the commercially available Spongostan® sponges and Surgifoam® sponges). The cross-linked sponges are micronised by methods known in the art to obtain a cross-linked biocompatible polymer in powder form, such as by rotary bed, extrusion, granulation and treatment in an intensive mixer, or milling (e.g. by using a hammer mill or a centrifugal mill).

Spongostan®/Surgifoam® available from Ethicon is a gelatine based cross-linked absorbable haemostatic sponge. It absorbs >35 g of blood/g and within 4-6 weeks it is completely absorbed in the human body.

The cross-linked powder particles are in one embodiment less than approximately 1000 microns in size, i.e. so that they are able to pass through a 1×1 mm sieve.

In one embodiment, the paste of the present invention comprises between about 10% to about 60% of the biocompatible polymer, for example about 10% to about 50% of the biocompatible polymer, such as about 10% to about 40% of the biocompatible polymer, for example about 10% to about 30% of the biocompatible polymer, such as about 12% to about 25% of the biocompatible polymer, for example about 14% to about 25% of the biocompatible polymer, such as about 15% to about 25% of the biocompatible polymer, for example about 16% to about 20% of the biocompatible polymer, such as about 17% to about 20% of the biocompatible polymer, for example about 18% to about 20% of the biocompatible polymer.

In one embodiment, the paste of the present invention comprises more than 10% of the biocompatible polymer, such as more than 15% of the biocompatible polymer, for example more than 16% of the biocompatible polymer, such as more than 17% of the biocompatible polymer, for example more than 18% of the biocompatible polymer, such as more than 19% of the biocompatible polymer, for example more than 20% of the biocompatible polymer.

In one embodiment, the paste of the present invention comprises less than 40% of the biocompatible polymer, such as less than 30% of the biocompatible polymer, for example less than 25% of the biocompatible polymer, such as less than 20% of the biocompatible polymer.

In a preferred embodiment, the paste of the present invention comprises between about 10% to about 30% of the biocompatible polymer, more preferred between about 15% to about 25% of the biocompatible polymer, such as about 20% of the biocompatible polymer.

After drying, the composition comprises between about 40% and 80% of the biocompatible polymer, such as between about 45% and 80% of the biocompatible polymer, for example between about 50% and 80% of the biocompatible polymer, such as between about 55% and 80% of the biocompatible polymer.

In one embodiment, the composition after drying comprises between about 40% and 80% of the biocompatible polymer, such as between about 45% and 75% of the biocompatible polymer, for example between about 50% and 70% of the biocompatible polymer.

In one embodiment, the dry composition of the present invention comprises more than about 30% of the biocompatible polymer, such as more than about 40% of the biocompatible polymer, for example more than about 45% of the biocompatible polymer, such as more than about 50% of the biocompatible polymer, for example more than about 55% of the biocompatible polymer, such as more than about 60% of the biocompatible polymer, for example more than about 65% of the biocompatible polymer, such as more than about 70% of the biocompatible polymer, for example more than about 75% of the biocompatible polymer, such as more than about 80% of the biocompatible polymer.

In one embodiment, the dry composition of the present invention comprises less than about 80% of the biocompatible polymer, such as less than about 70% of the biocompatible polymer, for example less than about 65% of the biocompatible polymer, such as less than about 60% of the biocompatible polymer, for example less than about 55% of the biocompatible polymer, such as less than about 50% of the biocompatible polymer.

Aqueous Medium

The aqueous medium of the present invention may be any aqueous medium suitable for preparing a paste suitable for haemostatic use known to a person of skill, e.g. water, saline, a calcium chloride solution or a buffered aqueous medium. The water may be WFI (Water For Injection). It is important that the aqueous medium is selected so that the reconstituted paste product is isotonic when intended for use on a human or animal subject.

The aqueous medium of the present invention is in one embodiment a saline solution.

The aqueous medium of the present invention is in one embodiment a calcium chloride solution.

In other embodiments, the aqueous medium is water.

The aqueous medium may also be a buffered aqueous medium suitable for use in a haemostatic paste. Any suitable buffering agent known to a person of skill may be used, such as one or more buffering agents selected from the group consisting of: Sodium citrate; Citric acid, Sodium citrate; Acetic acid, Sodium acetate; K2HPO4, KH2PO4; Na2HPO4, NaH2PO4; CHES; Borax, Sodium hydroxide; TAPS; Bicine; Tris; Tricine; TAPSO; HEPES; TES; MOPS; PIPES; Cacodylate; SSC; MES, or others. The pH of the buffered aqueous medium should be suitable for creating a haemostatic paste intended for human use and can be determined by the skilled person.

The amount of aqueous medium must be carefully adjusted to the amount of the biocompatible polymer for a haemostatic paste of a suitable consistency to form.

The paste of the present invention prior to drying comprises between about 50% and about 90% of water, such as between about 55% and about 85% of water, for example between about 60% and about 80% of water, such as about 70% of water.

Preferably, the paste of the present invention prior to drying comprises between about 60% and about 80%, more preferred about 70% to about 75% of water.

After drying, the dry composition comprises less than about 5% of water, such as less than about 3% of water, preferably less than about 2% of water, more preferred less than about 1.5% of water, even more preferred less than about 1% of water or even less. Hence, in one embodiment, the dry composition comprises from about 0.1 to about 5% water, such as from about 0.1% to about 2% water.

In one embodiment, the residual water content in the dry composition is about 0.5% or less. Such a low residual water content is possible with e.g. industrial freeze-drying apparatuses.

A low residual water content in the composition after drying is desirable as it decreases the risk of microbial growth in the dry composition. Furthermore, a low residual water content is essential if the composition comprises bioactive agents that are unstable in aqueous conditions, such as e.g. thrombin.

If thrombin is present in the composition of the present invention, the residual water content in the dried composition is preferably less than about 3% water, more preferred less than about 2% water.

Polyols

According to the invention, one or more polyols are added to the composition prior to drying the composition. The one or more polyols play a role in achieving a dry composition which upon addition of a liquid in the form of an aqueous medium such as water spontaneously reconstitutes to form a paste of an optimal consistency for haemostatic purposes without the use of mechanical mixing or stirring of any kind.

A polyol as defined herein is a compound with multiple hydroxyl functional groups. Polyols as defined herein include sugars (mono-, di- and polysaccharides) and sugar alcohols and derivatives thereof.

Monosaccharides include but are not limited to glucose, fructose, galactose, xylose and ribose.

Disaccharides include but are not limited to sucrose (saccharose), lactulose, lactose, maltose, trehalose and cellobiose.

Polysaccharides include but are not limited to starch, glycogen, cellulose and chitin.

A sugar alcohol, also known as a polyalcohol is a hydrogenated form of carbohydrate, whose carbonyl group (aldehyde or ketone, reducing sugar) has been reduced to a primary or secondary hydroxyl group (hence the alcohol). Sugar alcohols have the general formula $H(HCHO)_{n+1}H$, whereas sugars have $H(HCHO)_nHCO$. Some common sugar alcohols which may be used in the method of the present invention include but are not limited to: Glycol (2-carbon), Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Dulcitol (6-carbon), Fucitol (6-carbon), Iditol (6-carbon), Inositol (6-carbon; a cyclic sugar alcohol), volemitol (7-carbon), Isomalt (12-carbon), Maltitol (12-carbon), Lactitol (12-carbon), Polyglycitol.

In one embodiment, the composition comprises a single polyol.

In one embodiment of the invention, the composition comprises more than one polyol, such as two, three, four, five, six or even more different polyols.

In one embodiment of the invention, the composition comprises two polyols, for example mannitol and glycerol or trehalose and a glycol.

In one embodiment of the invention, the composition comprises one or more sugar alcohols, such as one or more sugar alcohols selected from the group consisting of Glycol, Glycerol, Erythritol, Threitol, Arabitol, Xylitol, Ribitol, Mannitol, Sorbitol, Dulcitol, Fucitol, Iditol, Inositol, volemitol, Isomalt, Maltitol, Lactitol and Polyglycitol.

In one embodiment, the composition comprises one or more sugar alcohols and one or more sugars, such as one sugar alcohol and one sugar.

In one embodiment, the composition comprises one sugar alcohol and optionally one or more additional polyols, which may be either sugar alcohols or sugars.

In one embodiment, the composition does not comprise a sugar as the only polyol.

In one embodiment of the invention, the composition comprises mannitol.

In one embodiment of the invention, the composition comprises sorbitol.

In one embodiment of the invention, the composition comprises glycerol.

In one embodiment of the invention, the composition comprises trehalose.

In one embodiment of the invention, the composition comprises glycol, such as propylene glycol.

In one embodiment of the invention, the composition comprises xylitol.

In one embodiment of the invention, the composition comprises maltitol.

In one embodiment of the invention, the composition comprises sorbitol.

In one embodiment the paste according to the invention prior to drying comprises from about 1% to about 40% of one or more polyols, for example from about 1% to about 30% of one or more polyols, such as from about 1% to about 25% of one or more polyols, for example from about 1% to about 20% of one or more polyols, such as from about 1% to about 15% of one or more polyols, such as from about 1% to about 14% of one or more polyols, for example from about 1% to about 13% of one or more polyols, such as from about 1% to about 12% of one or more polyols, for example from about 1% to about 11% of one or more polyols, such as about 1% to about 10% of one or more polyols.

In one embodiment the paste according to the invention prior to drying comprises from about 2% to about 40% of one or more polyols, for example from about 2% to about 30% of one or more polyols, such as from about 2% to about 25% of one or more polyols, for example from about 2% to about 20% of one or more polyols, such as from about 2% to about 18% of one or more polyols, for example from about 2% to about 17% of one or more polyols, such as from about 2% to about 16% of one or more polyols, for example from about 2% to about 15% of one or more polyols, such as from about 2% to about 14% of one or more polyols, for example from about 2% to about 13% of one or more polyols, such as from about 2% to about 12% of one or more polyols, for example from about 2% to about 11% of one or more polyols, such as about 2% to about 10% of one or more polyols.

In one embodiment the paste according to the invention prior to drying comprises from about 3% to about 40% of one or more polyols, for example from about 3% to about 30% of one or more polyols, such as from about 3% to about 25% of one or more polyols, for example from about 3% to about 20% of one or more polyols, such as from about 3% to about 18% of one or more polyols, for example from about 3% to about 17% of one or more polyols, such as from about 3% to about 16% of one or more polyols, for example from about 3% to about 15% of one or more polyols, such as from about 3% to about 14% of one or more polyols, for example from about 3% to about 13% of one or more polyols, such as from about 3% to about 12% of one or more polyols, for example from about 3% to about 11% of one or more polyols, such as about 3% to about 10% of one or more polyols.

In one embodiment, the paste according to the invention prior to drying comprises more than about 5% of one or more polyols, hence in one embodiment the paste according to the invention prior to drying comprises from about 5% to about 40% of one or more polyols, for example from about 5% to about 30% of one or more polyols, such as from about 5% to about 25% of one or more polyols, for example from about 5% to about 20% of one or more polyols, such as from about 5% to about 18% of one or more polyols, for example from about 5% to about 17% of one or more polyols, such as from about 5% to about 16% of one or more polyols, for example from about 5% to about 15% of one or more polyols, such as from about 5% to about 14% of one or more polyols, for example from about 5% to about 13% of one or more polyols, such as from about 5% to about 12% of one or more polyols, for example from about 5% to about 11% of one or more polyols, such as about 5% to about 10% of one or more polyols.

In one embodiment the paste according to the invention prior to drying comprises from about 6% to about 40% of one or more polyols, for example from about 6% to about 30% of one or more polyols, such as from about 6% to about 25% of one or more polyols, for example from about 6% to about 20% of one or more polyols, such as from about 6% to about 18% of one or more polyols, for example from about 6% to about 17% of one or more polyols, such as from about 6% to about 16% of one or more polyols, for example from about 6% to about 15% of one or more polyols, such as from about 6% to about 14% of one or more polyols, for example from about 6% to about 13% of one or more polyols, such as from about 6% to about 12% of one or more polyols, for example from about 6% to about 11% of one or more polyols, such as about 6% to about 10% of one or more polyols.

In one embodiment the paste according to the invention prior to drying comprises from about 10% to about 40% of one or more polyols, for example from about 10% to about 30% of one or more polyols, such as from about 10% to about 25% of one or more polyols, for example from about 10% to about 20% of one or more polyols, such as from about 10% to about 18% of one or more polyols, for example from about 10% to about 17% of one or more polyols, such as from about 10% to about 16% of one or more polyols, for example from about 10% to about 15% of one or more polyols.

In one embodiment, the paste according to the invention prior to drying comprises more than about 1% of one or more polyols, such as more than about 2% of one or more polyols, for example more than about 3% of one or more polyols, such as more than about 4% of one or more polyols, for example more than about 5% of one or more polyols, such as more than about 6% of one or more polyols, for example more than about 7% of one or more polyols, such as more than about 8% of one or more polyols, for example more than about 9% of one or more polyols, such as more than about 10% of one or more polyols.

In one embodiment, the paste according to the invention prior to drying comprises less than about 20% of one or more polyols, such as less than about 18% of one or more polyols, for example less than about 17% of one or more polyols, such as less than about 16% of one or more polyols, for example less than about 15% of one or more polyols, such as less than about 14% of one or more polyols, for example less than about 13% of one or more polyols, such as less than about 12% of one or more polyols, for example less than about 11% of one or more polyols, such as less than about 10% of one or more polyols.

After drying, the dry composition comprises from about 10% to about 60% of one or more polyols, such as from about 20% to about 50% of one or more polyols, for example from about 20% to about 50%, such as from about 20% to about 45% of one or more polyols, for example from about 20% to about 40%, such as from about 20% to about 35% of one or more polyols, for example from about 20% to about 30% of one or more polyols.

In one embodiment, the dry composition comprises from about 20% to about 60% of one or more polyols, such as from about 20% to about 50% of one or more polyols, for example from about 20% to about 50%, such as from about 20% to about 45% of one or more polyols, for example from about 20% to about 40%, such as from about 20% to about 30% of one or more polyols.

In one embodiment, the dry composition comprises from about 25% to about 60% of one or more polyols, such as from about 25% to about 50% of one or more polyols, for example from about 25% to about 45% of one or more polyols, such as from about 25% to about 40% of one or more polyols, for example from about 25% to about 35% of one or more polyols, such as from about 25% to about 30% of one or more polyols.

In one embodiment, the dry composition comprises from about 27% to about 60% of one or more polyols, such as from about 27% to about 50% of one or more polyols, for example from about 27% to about 45% of one or more polyols, such as from about 27% to about 40% of one or more polyols, for example from about 27% to about 35% of one or more polyols, such as from about 27% to about 30% of one or more polyols.

In one embodiment, the dry composition comprises from about 30% to about 60% of one or more polyols, such as from about 30% to about 50% of one or more polyols, for example from about 30% to about 45% of one or more polyols, such as from about 30% to about 40% of one or more polyols, for example from about 30% to about 35% of one or more polyols.

In one embodiment, the dry composition comprises less polyol than biocompatible polymer, i.e. the polyol:biocompatible polymer ratio is less than 1:1, such as less than or about 0.9:1, for example less than or about 0.8:1, such as less than or about 0.7:1, for example less than or about 0.6:1, such as less than or about 0.5:1, such as less than or about 0.4:1, for example less than or about 0.3:1, such as less than or about 0.2:1, for example less than or about 0.1:1. The polyol:biocompatible polymer ratio is the same in the paste prior to drying.

In one embodiment, the polyol:biocompatible polymer ratio is between about 0.1:1 and 1:1; such as between about 0.2:1 and 1:1, for example between about 0.3:1 and 1:1, such as between about 0.4:1 and 1:1.

In a preferred embodiment, the polyol:biocompatible polymer ratio is between about 0.2:1 and 0.8:1; such as between about 0.2:1 and 0.7:1, for example between about 0.2:1 and 0.6:1, such as between about 0.2:1 and 0.5:1. Even more preferred, the polyol:biocompatible polymer ratio is between about 0.3:1 and 0.8:1; such as between about 0.3:1 and 0.7:1, for example between about 0.3:1 and 0.6:1, such as between about 0.3:1 and 0.5:1, for example between about 0.35:1 and 0.5:1, such as between about 0.35:1 and 0.45:1.

In one embodiment the polyol of the present invention is not polyethylene glycol.

Bioactive Agent

In one embodiment of the invention, the dry composition comprises one or more bioactive agents. It is essential that the bioactive agent retains its bioactivity, i.e. that the bioactive agent is biologically active in the paste after reconstitution of the dry composition. Many bioactive agents are unstable in solution, particularly enzymes and other proteins that may be degraded or lose their secondary structure when water is present.

In one embodiment the bioactive agent stimulates wound healing and/or haemostasis, such as thrombin.

Conventionally, a thrombin solution is added to a gelatine powder to make a haemostatic paste directly at the surgical site at the time of need of the haemostatic paste, e.g. by using commercially available haemostatic kits such as Floseal and Surgiflo®. The thrombin solution must be made just prior to making the paste as thrombin in solution is very unstable and will self-degrade rapidly. The making of a thrombin solution at the surgical site is time consuming and involves a risk of making mistakes regarding the correct dilution of thrombin.

The present invention allows for the addition of thrombin to a paste prior to drying, thereby resulting in a dry composition comprising thrombin, which upon reconstitution with a suitable aqueous medium, such as water, will comprise a desired amount of thrombin without the need for time-consuming and error-prone thrombin dilution steps and addition at the surgical site. That thrombin may be included in the dry composition of the present invention thus constitutes a clear advantage over conventional methods for making haemostatic pastes.

The present inventor has shown that thrombin may be included in a paste and dried by freeze-drying according to the present invention with essentially no loss of thrombin activity measured in the reconstituted paste.

Thrombin may be added to the paste of the present invention prior to drying at a concentration in the range of about 100 IU/ml paste to about 500 IU/ml paste, such as about 150 IU/ml paste to about 450 IU/ml paste, for example about 200 IU/ml paste to about 400 IU/ml paste, such as about 250 IU/ml paste to about 350 IU/ml paste.

In one embodiment, the one or more bioactive agents can be e.g. thrombin or thrombin in combination with fibrinogen, or thrombin and fibrinogen in combination with Factor XIII, or thrombin and fibrinogen and Factor XIII in combination with tranexamic acid.

Thrombin is a "trypsin-like" serine protease protein that in humans is encoded by the F2 gene. Prothrombin (coagulation factor II) is proteolytically cleaved to form thrombin in the coagulation cascade, which ultimately results in the stemming of blood loss. Thrombin in turn acts as a serine protease that converts soluble fibrinogen into insoluble strands of fibrin, as well as catalyzing many other coagulation-related reactions. In the blood coagulation pathway, thrombin acts to convert factor XI to XIa, VIII to VIIIa, V to Va, and fibrinogen to fibrin.

A preferred bioactive agent according to the invention is thrombin. In one embodiment, the thrombin is added as prothrombin.

In one embodiment, the dry composition comprises one or more bioactive agents that stimulate bone and/or tendon healing such as one or more growth factors selected from the group consisting of matrix metalloproteinases (MMPs), insulin-like growth factor 1 (IGF-I), platelet-derived growth factor (PDGF), vascular endothelial growth factor (VEGF), basic fibroblast growth factor (bFGF) and transforming growth factor beta (TGF-β).

In one embodiment, the dry composition comprises one or more Bone Morphogenetic Proteins (BMPs). Bone morphogenetic proteins (BMPs) are a subgroup of the TGF-β superfamily. Bone Morphogenetic Proteins (BMPs) are a group of growth factors also known as cytokines and as metabologens. Originally discovered by their ability to induce the formation of bone and cartilage, BMPs are now considered to constitute a group of pivotal morphogenetic signals, orchestrating tissue architecture throughout the body.

In one embodiment, the dry composition comprises one or more matrix metalloproteinases (MMPs). MMPs are zinc-dependent endopeptidases. MMPs have a very important role in the degradation and remodeling of the extracellular matrix (ECM) during the healing process after an injury. Certain MMPs including MMP-1, MMP-2, MMP-8, MMP-13, and MMP-14 have collagenase activity, meaning that, unlike many other enzymes, they are capable of degrading collagen I fibrils.

These growth factors all have different roles during the healing process. IGF-1 increases collagen and proteoglycan production during the first stage of inflammation, and PDGF is also present during the early stages after injury and promotes the synthesis of other growth factors along with the synthesis of DNA and the proliferation of cells. The three isoforms of TGF-β (TGF-β1, TGF-β2, TGF-β3) are known to play a role in wound healing and scar formation. VEGF is well known to promote angiogenesis and to induce endothelial cell proliferation and migration.

In one embodiment, the dry composition of the present invention comprises flakes or particles of extracellular matrix (ECM). ECM is the extracellular part of animal tissue that usually provides structural support to the animal cells in addition to performing various other important functions. ECM has been shown to have very beneficial effect in healing as it facilitates functional tissue regeneration.

The variety of biological agents that can be used in conjunction with the paste of the invention is vast. In general, biological agents which may be administered via the compositions of the invention include, without limitation, antiinfectives, such as antibiotics and antiviral agents; analgesics and analgesic combinations; antihelmintics; antiarthritics; anticonvulsants; antidepressants; antihistamines; antiinflammatory agents; antimigraine preparations; antineoplastics; antiparkinsonism drugs; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; hormones, such as estradiol and other steroids, including corticosteroids; immunosuppressives; muscle relaxants; parasympatholytics; psychostimulants; naturally derived or genetically engineered proteins, polysaccharides, glycoproteins, or lipoproteins; oligonucleotides, antibodies, antigens, cholinergics, chemotherapeutics, radioactive agents, osteoinductive agents, cystostatics heparin neutralizers, procoagulants and hemostatic agents, such as prothrombin, thrombin, fibrinogen, fibrin, fibronectin, heparinase, Factor X/Xa, Factor VII/VIIa, Factor VIII/VIIIa, Factor IX/IXa, Factor XI/XIa, Factor XII/XIIa, Factor XIII/XIIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents and synthetic peptides having haemostatic activity.

Further Compounds

The dry composition of the invention may further comprise one or more of the following: DMSO (dimethyl sulfoxide), 2-Methyl-2,4-pentanediol (MPD) and/or one or more of the compounds mentioned in the table below.

| Bulking agent | Buffering agent | Solubilising agent | Miscellaneous |
| --- | --- | --- | --- |
| Sugars/Sugar alcohols: Mannitol Lactose Sucrose Trehalose Sorbitol Glucose Raffinose | Citric acid Sodium citrate Potassium citrate Tartaric acid Sodium phosphate Tris base Tris HCl Tris acetate Zinc chloride Sodium acetate Potassium acetate Arginine | Complexing agent: Ethylediamine tetra acetic acid (EDTA) Alpha cyclodextrin Hydroxypropyl-β-cyclodextrin (HP-β-CD) | Tonicifying agent: Sodium chloride Sucrose Mannitol Dextrose |
| Amino acids: Arginine Glycine Histidine | pH adjusting agent: Hydrochloric acid Sodium hydroxide Meglumine | Surfactants: polysorbate 80 | Antimicrobial agents: Benzalkonium chloride benzyl alcohol phenol m-cresol methyl paraben ethyl paraben |
| Polymer: Dextran Polyethylene glycol | | Co-solvents: Tert-butyl alcohol Iso-propyl alcohol Dichloromethane Ethanol Acetone Glycerol | Collapse temperature modifier: Dextran Hydroxyethyl starch Ficoll gelatin |

In one embodiment, the dry composition of the present invention comprises one or more antimicrobial agents, such as one or more antibacterial agents.

In one embodiment, the dry composition of the present invention comprises benzalkonium chloride.

In one embodiment, the dry composition of the present invention does not comprise an antimicrobial agent.

Making a Paste

According to the method of the invention, the biocompatible polymer and the one or more polyols are mixed with a suitable aqueous medium to obtain a paste. The mixing may be performed in any suitable way known to a person of skill, e.g. by mixing the contents manually or by using an electrical mixing apparatus, such as a hand mixer, a kitchen mixer or an industrial mixer.

Mixing of the paste can generally be performed at room temperature (20-25° C.). However, if thrombin or other enzymes are included in the paste, it is advisable to perform the mixing of the paste at chilled temperatures and/or within a short time period to avoid or decrease the proteolytic activity of thrombin, as it is well-known that thrombin is liable to self-degradation in solution. Hence, when thrombin or other proteolytic enzymes are to be included in the paste, the mixing of the paste is usually performed at temperatures below room temperature, such as at about 2° C. to about 20° C., for example at about 2° C. to about 15° C., preferably at about 4° C.

Another or an additional way of preserving the thrombin bioactivity in the paste is to keep the time that thrombin is in a wet state, i.e. the mixing time, at a minimum. Hence, when thrombin or other proteolytic enzymes are to be included in the paste, the mixing of the paste is usually performed within about 5 minutes to about 10 hours, such as about 5 minutes to about 5 hours, for example about 5 minutes to about 2 hours, preferably about 5 minutes to about 1 hour.

The inventor of the present application has found that it is not essential to perform the mixing of the paste at low temperatures to avoid loss of thrombin activity as no decrease in thrombin activity was discovered when mixing of the paste was performed at ambient temperatures.

Containers

Any suitable container known to a person of skill may be used for preparing the paste and holding the paste of the present invention while drying, such as vials, jars, tubes, trays, cartridges or syringes.

In one embodiment, the paste is prepared in one container and transferred to another container for drying, wherein said container may be selected from a vial, a jar, a tube, a tray, a cartridge and a syringe.

A "jar" according to the invention is a rigid, approximately cylindrical container with a wide mouth opening. Jars may comprise a re-closable closure unit/lid applied to the mouth of the jar.

The containers may be made from any suitable material such as glass, ceramic, plastic or metal, such as stainless steel.

Examples of suitable plastic materials include but are not limited to polyethylene, polypropylene, polystyrene, polyvinyl chloride, and polytetrafluoroethylene (PTFE).

In one embodiment, the paste is filled into and dried within a syringe or other known applicators suitable for dispensing flowable haemostatic compositions.

The dry composition of the present invention may be prepared in various shapes, forms and sizes depending on the shape of the container used. They may be e.g. in the form of plugs, disks, rods, tubes, conical cylinders, sheets, spheres, half spheres, tablets, pellets, granules, or even fine particulates or powders (pulverised).

Haemostatic Sheet

In one embodiment the dry composition is in the form of a sheet, i.e. a substantially flat composition.

A dry composition in the form of a sheet may be obtained by spreading the paste of the invention thinly and evenly on a surface followed by drying of the paste to obtain a substantially flat dry sheet composition. A dry composition in the form of a sheet will upon contact with a liquid reconstitute spontaneously to form a paste. Thus, a dry composition in the form of a sheet has the advantages of both traditionally used surgical sponges in that it can cover relatively large areas and the advantage of a paste in that it conforms easily to uneven surfaces upon wetting.

The dry composition in the form of a sheet is soft and flexible.

In one embodiment the invention relates to a dry composition in the form of a sheet for use in haemostasis and/or wound healing.

In one embodiment, the sheet is not pre-wetted before use, i.e. before application to a wound.

The height of the dry sheet composition is in one embodiment between about 0.5 mm and about 10 mm, preferably between about 1 mm and 5 mm, more preferred between about 1 mm and 3 mm, such as about 2 mm.

The size (width and depth) of the dry sheet composition depends on the intended use of the sheet and can be selected by the skilled person. The dry sheet material may e.g. be rectangular, square or circular. For example, the dry sheet composition may e.g. be in the form of a rectangle of approximately 5 cm×10 cm, 2 cm×6 cm, 6 cm×8 cm or 8 cm×12 cm.

In one embodiment, the dry sheet composition is cut into the desired shape prior to use.

Drying the Paste

According to the invention the paste is dried to obtain the dry composition. The paste may be dried by any suitable methods known to a person of skill. Examples of suitable drying methods include freeze-drying and spray drying.

In one embodiment, the paste is frozen prior to the drying step.

In a preferred embodiment, the paste is freeze-dried. Any suitable freeze-drying technique and equipment known to the person of skill may be used.

Freeze-drying (also known as lyophilisation and cryodesiccation) is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

There are essentially three categories of freeze-dryers: the manifold freeze-dryer, the rotary freeze-dryer and the tray style freeze-dryer. Two components are common to all types of freeze-dryers: a vacuum pump to reduce the ambient gas pressure in a vessel containing the substance to be dried and a condenser to remove the moisture by condensation on a surface cooled to −40 to −80° C. The manifold, rotary and tray type freeze-dryers differ in the method by which the dried substance is interfaced with a condenser. In manifold freeze-dryers a short usually circular tube is used to connect multiple containers with the dried product to a condenser. The rotary and tray freeze-dryers have a single large reservoir for the dried substance.

Rotary freeze-dryers are usually used for drying pellets, cubes and other pourable substances. The rotary dryers have a cylindrical reservoir that is rotated during drying to achieve a more uniform drying throughout the substance. Tray style freeze-dryers usually have rectangular reservoir with shelves on which products, such as pharmaceutical solutions and tissue extracts, can be placed in trays, vials and other containers.

Manifold freeze-dryers are usually used in a laboratory setting when drying liquid substances in small containers and when the product will be used in a short period of time. A manifold dryer will dry the product to less than 5% moisture content. Without heat, only primary drying (removal of the unbound water) can be achieved. A heater must be added for secondary drying, which will remove the bound water and will produce a lower moisture content.

Tray style freeze-dryers are typically larger than the manifold dryers and are more sophisticated. Tray style freeze-dryers are used to dry a variety of materials. A tray freeze-dryer is used to produce the driest product for long-term storage. A tray freeze-dryer allows the product to be frozen in place and performs both primary (unbound water removal) and secondary (bound water removal) freeze-drying, thus producing the driest possible end-product. Tray freeze-dryers can dry products in bulk or in vials or other containers. When drying in vials, the freeze-drier is supplied with a stoppering mechanism that allows a stopper to be pressed into place, sealing the vial before it is exposed to the atmosphere. This is used for long-term storage, such as vaccines.

Improved freeze drying techniques are being developed to extend the range of products that can be freeze dried, to improve the quality of the product, and to produce the product faster with less labour.

Ever since the 1930s, industrial freeze drying has been dependent on a single type of equipment: the tray freeze drier. In 2005 a quicker and less-labour intensive freeze drying method was developed for bulk materials. This freeze drying process proved to be able to produce free-flowing powder from a single vessel. Known as [Active Freeze Drying] AFD technology, the new process used continuous motion to improve mass transfer and hence cutting processing time, while also eliminating the need to transfer to and from drying trays and downstream size reduction devices.

There are four stages in the complete freeze-drying process: pre-treatment, freezing, primary drying, and secondary drying.

Pre-treatment includes any method of treating the product prior to freezing. This may include concentrating the product, formulation revision (i.e., addition of components to increase stability and/or improve processing), decreasing a high vapor pressure solvent or increasing the surface area. In many instances the decision to pre-treat a product is based on theoretical knowledge of freeze-drying and its requirements, or is demanded by cycle time or product quality considerations. Methods of pre-treatment include: Freeze concentration, Solution phase concentration, Formulation to Preserve Product Appearance, Formulation to Stabilize Reactive Products, Formulation to Increase the Surface Area, and Decreasing High Vapor Pressure Solvents.

In a lab, freezing is often done by placing the material in a freeze-drying flask and rotating the flask in a bath, called a shell freezer, which is cooled by mechanical refrigeration, dry ice and methanol, or liquid nitrogen. On a larger scale, freezing is usually done using a freeze-drying machine. In this step, it is important to cool the material below its triple point, the lowest temperature at which the solid and liquid phases of the material can co-exist. This ensures that sublimation rather than melting will occur in the following steps. Larger crystals are easier to freeze-dry. To produce larger crystals, the product should be frozen slowly or can be cycled up and down in temperature. This cycling process is called annealing. In other cases it is better that the freezing is done rapidly, in order to lower the material to below its eutectic temperature quickly, thus avoiding the formation of ice crystals. Usually, the freezing temperatures are between −40° C. and −80° C. The freezing phase is the most critical in the whole freeze-drying process, because the product can be spoiled if badly done.

Amorphous materials do not have a eutectic point, but they do have a critical point, below which the product must be maintained to prevent melt-back or collapse during primary and secondary drying.

During the primary drying phase, the pressure is lowered (to the range of a few millibars or less), and enough heat is supplied to the material for the water to sublime. The amount of heat necessary can be calculated using the sublimating molecules' latent heat of sublimation. In this initial drying phase, about 95% of the water in the material is sublimated. This phase may be slow (can be several days in the industry), because, if too much heat is added, the material's structure could be altered.

In this phase, pressure is controlled through the application of partial vacuum. The vacuum speeds sublimation, making it useful as a deliberate drying process. Furthermore, a cold condenser chamber and/or condenser plates provide a surface(s) for the water vapour to re-solidify on. This condenser plays no role in keeping the material frozen; rather, it prevents water vapor from reaching the vacuum pump, which could degrade the pump's performance. Condenser temperatures are typically below −50° C.

It is important to note that, in this range of pressure, the heat is brought mainly by conduction or radiation; the convection effect is negligible, due to the low air density.

The vapour pressure of water is the pressure at which water vapour is saturated. At higher pressures water would condense. The water vapour pressure is the partial pressure of water vapour in any gas mixture saturated with water. The water vapour pressure determines the temperature and pressure necessary for freeze-drying to occur.

Vapour pressure of water (mTorr=millitorr; mB=millibar)

| Temp (C.) | mTorr | mB |
|---|---|---|
| 0 | 4579 | 6.104 |
| −4 | 3280 | 4.372 |
| −8 | 2326 | 3.097 |
| −12 | 1632 | 2.172 |
| −16 | 1132 | 1.506 |
| −20 | 930 | 1.032 |
| −24 | 526 | 0.6985 |
| −28 | 351 | 0.4669 |
| −32 | 231 | 0.3079 |
| −36 | 150 | 0.2020 |
| −40 | 96.6 | 0.1238 |
| −44 | 60.9 | 0.0809 |
| −48 | 37.8 | 0.0502 |
| −52 | 23.0 | 0.0300 |
| −56 | 13.8 | 0.0183 |
| −60 | 8.0 | 0.0107 |
| −64 | 4.6 | 0.0061 |
| −68 | 2.6 | 0.0034 |
| −72 | 1.4 | 0.0018 |

The secondary drying phase aims to remove unfrozen water molecules, since the ice was removed in the primary drying phase. This part of the freeze-drying process is governed by the material's adsorption isotherms. In this phase, the temperature is raised higher than in the primary drying phase, and can even be above 0° C., to break any physico-chemical interactions that have formed between the water molecules and the frozen material. Usually the pressure is also lowered in this stage to encourage desorption (typically in the range of microbars). However, there are products that benefit from increased pressure as well.

After the freeze-drying process is complete, the vacuum may be broken with an inert gas, such as nitrogen, before the material is sealed.

At the end of the operation, the final residual water content in the freeze-dried product is in general very low, such as around 2% or lower.

The freeze-drying process transforms the paste into a hard "cake-like" composition, which upon addition of an adequate amount of an aqueous medium, such as water, will form a ready-to use paste spontaneously, i.e. no mechanical mixing/reconstitution is required for said paste to form.

In one embodiment, the hard cake-like structure obtained by freeze-drying the paste is pulverised before addition of the aqueous medium. Upon addition of the aqueous medium, a ready-to-use paste will form spontaneously.

In an alternative embodiment, the dry composition of the present invention is obtained by spray-drying. Any spray drying technique and equipment known to the skilled person may be applied.

Spray drying is a method of producing a dry powder from a liquid or slurry by rapidly drying with a hot gas. Air is usually the heated drying media; however, if the liquid is a flammable solvent such as ethanol or the product is oxygen-sensitive then nitrogen is used.

All spray dryers use some type of atomizer or spray nozzle to disperse the liquid or slurry into a controlled drop size spray. The most common of these are rotary disks and single-fluid high pressure swirl nozzles. Alternatively, for some applications two-fluid or ultrasonic nozzles are used. Depending on the process needs, drop sizes from 10 to 500 µm can be achieved with the appropriate choices. The most common applications are in the 100 to 200 µm diameter range. The dry powder obtained is often free-flowing.

Spray dryers can dry a product very quickly compared to other methods of drying. They also turn a solution or slurry into a dried powder in a single step, which can be advantageous for profit maximization and process simplification.

The dry powdered composition obtained by spray-drying may be reconstituted without the use of any mechanical mixing, i.e. a paste will form spontaneously upon addition of a suitable amount of liquid.

Outer Packaging

In one embodiment the dry composition contained within e.g. a syringe or other containment unit, is further contained within an outer packaging so that the dry product is kept sterile until use. This will allow the user to remove the outer packaging and transfer the dry composition into a sterile field. Here a suitable amount of aqueous medium can be added, whereupon a ready-to-use paste forms spontaneously within seconds without any need for mechanical agitation, stirring or mixing.

The outer packaging is usually made from a flexible, semi-rigid or rigid material and typically consists of materials such as plastic, aluminium foil and/or plastic laminate, where the plastic may be selected from the group consisting of PET, PETG, PE, LLDPE, CPP, PA, PETP, METPET, Tyvek and optionally bonded with an adhesive, such as polyurethane, or co-extruded.

In one embodiment, the outer packaging is an aluminium foil outer packaging.

The outer packaging preferably forms a complete barrier to moisture.

The outer packaging is preferably able to endure sterilisation treatment such as by radiation.

Sterilisation

The dry composition of the present invention is preferably sterile. Any suitable sterilisation technique known in the art may be utilised. The sterilisation preferably occurs after the packaging step, i.e. when the dry composition is contained within an outer packaging. Thus, in a preferred embodiment sterilisation is terminal sterilisation.

Sterilisation refers to any process that effectively kills or eliminates transmissible agents (such as fungi, bacteria, viruses, prions and spore forms etc.). Sterilisation of the dry composition can be achieved through e.g. application of heat, chemicals, and irradiation. Heat sterilization include autoclaving (uses steam at high temperatures) and dry heat; radiation sterilisation include X-rays, gamma and beta rays, UV light and subatomic particles; chemical sterilisation include using ethylene oxide gas, ozone, chlorine bleach, glutaraldehyde, formaldehyde, ortho phthalaldehyde, hydrogen peroxide and peracetic acid.

In one embodiment, the dry composition is sterilised by irradiation, e.g. ionizing irradiation, so as to provide sterility to the composition. Such irradiation may include e-beam (beta irradiation) or gamma irradiation. The level of irradiation and conditions for sterilisation, including the time that the composition is irradiated, are those that provide sterile compositions. Sterilisation conditions are similar to those currently utilized in the preparation of haemostatic loose powders currently available. Once having the benefit of this disclosure, one skilled in the art will be able to readily determine the level of irradiation necessary to provide sterile compositions.

When thrombin and/or other sensitive bioactive agents are present in the dried product, sterilisation is usually performed as terminal sterilisation with about 25 kGy or less of beta or gamma irradiation.

In one embodiment, sterilisation is performed with ethylene oxide.

Sterilisation with dry heat may typically be carried out by heating the dry composition to a temperature between 100° C. and 250° C., such as about 110° C. to about 200° C. In particular the temperature may be in the range of 110-160° C., e.g. in the range of 110-140° C., or in the range of 120-180° C., or in the range of 130-170° C., or in the range of 130-160° C., or in the range of 120-150° C.

In one embodiment, the dry composition is not sterilised after packaging. When the dry composition is manufactured by aseptic production techniques, the product is already sterile when placed in the outer packaging and no further sterilisation is required. Thus, in one embodiment the present invention relates to a composition produced by aseptic techniques.

Medical Use

The present invention further relates to use of the paste obtained from the dry composition for promoting haemostasis and/or wound healing.

The paste of the present invention may e.g. be used in an array of surgical procedures wherein bleeding control is desired. A paste conforms to irregular surfaces to stop bleeding fast and it is therefore useful for providing rapid haemostasis on rough or uneven surfaces where haemostatic sponges are not efficient.

Haemostatic pastes are prepared directly at the surgical site at the time of need by the medical practitioner, i.e. doctors or nurses. The paste is thus often prepared under extremely stressful conditions and it is therefore essential that the process for preparing the paste is simple and fast to ensure that the bleeding is arrested as quickly as possible and that no mistakes are made while preparing the paste. It is also important that the consistency of the paste is suitable for use as a haemostatic paste.

The paste of the present invention is superior to currently available pastes such as Floseal and Surgiflo due to the fact that the paste of the present invention may be prepared simply by adding an amount of an aqueous medium to the dry composition, whereupon a ready-to-use haemostatic paste forms spontaneously, i.e. within less than about 30 seconds, preferably within less than about 20 seconds, more preferred within less than about 10 seconds, even more preferred within less than about 5 seconds.

The quantity of liquid to be added to the dry composition may be adjusted by the skilled person. The paste so formed always has an optimal consistency when the correct amount of liquid is added. This is not the case with the conventional pastes, where the consistency of the paste depends heavily on the force applied and time spent mixing. That no mechanical mixing is required also means that less time is spent preparing the paste, which in turn leads to increased patient safety, both due to the fact that the haemostatic paste can be applied to the patient faster and that the simple preparation method decreases the likelihood of mistakes being made during the preparation of the haemostatic paste.

When thrombin is comprised within the dry composition, the invention further has the advantage over conventional pastes in that it avoids the time-consuming and error-prone thrombin dilution and addition steps involved in current methods for making haemostatic pastes.

In one embodiment the present invention relates to a method for arresting bleeding/promoting haemostasis in an individual in need thereof by application of the reconstituted paste of the present invention to the site of bleeding.

The paste of the present invention may be used for any type of surgery including general surgery, cardiothoracic surgery, vascular surgery, plastic surgery, pediatric surgery, colorectal surgery, transplant surgery, surgical oncology, trauma surgery, endocrine surgery, breast surgery, skin surgery, otolaryngology, gynecology, oral and maxillofacial surgery, dental Surgery, orthopedic surgery, neurosurgery, ophthalmology, podiatric surgery, urology.

In one embodiment the present invention relates to a method for promoting wound healing in an individual in need thereof by application of the paste of the present invention to the wound.

A "wound" refers broadly to injuries to the skin and/or underlying (subcutaneous) tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The present invention relates to treatment of any type of wound mentioned above using the paste of the present invention.

The treatment of a wound can in principle result in healing of the wound or in accelerated healing of the wound. The accelerated healing can be a result of e.g. administration of a wound-healing promoting substance. Alternatively, the wound healing can be promoted by preventing bacterial or viral infection, or by reducing the risk of such an infection which would otherwise have prolonged the wound treatment process.

In one embodiment the present invention relates to a method for promoting bone and/or tendon and/or tissue healing in an individual in need thereof by application of the paste of the present invention to the injured bone, tendon or tissue.

The "individual" referred to herein may be any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

A Haemostatic Kit

The present invention further relates to a haemostatic kit comprising the dry composition of the present invention and an amount of aqueous medium matched to the amount of the dry composition so that upon addition of the aqueous medium, a haemostatic paste of a consistency suitable for use as a haemostatic paste will form spontaneously, i.e. within seconds.

Hence, in one embodiment the present invention relates to a haemostatic kit comprising:
 a) a container comprising the dry composition obtained by the method of the present invention,
 b) a container comprising an aqueous medium, and
 c) optionally an outer packaging.

The aqueous medium used to reconstitute the paste may be e.g. be selected from water, saline, a $CaCl_2$ solution or a buffered aqueous solution.

In one embodiment, the aqueous medium used to reconstitute the dry composition is water. Preferably, the isotonicity of the aqueous medium is selected so that an isotonic paste will form upon addition of the aqueous medium to the dry composition.

In one embodiment, the aqueous medium used to reconstitute the dry composition is saline.

In one embodiment, the dry composition comprises thrombin.

Items

1. A method of preparing a dry haemostatic composition comprising the successive steps of:
    a. providing a haemostatic agent in powder form, one or more polyols and an aqueous medium,
    b. mixing the haemostatic agent, the one or more polyols and the aqueous medium to obtain a paste, and
    c. drying the paste.

2. The method according to item 1, wherein the haemostatic agent is gelatine.

3. The method according to any of the preceding items, wherein the haemostatic agent is cross-linked.

4. The method according to any of the preceding items, wherein the paste prior to drying comprises from about 2% to about 40% of one or more polyols, for example from about 2% to about 30% of one or more polyols, such as from about 2% to about 25% of one or more polyols, for example from about 2% to about 20% of one or more polyols, such as from about 2% to about 18% of one or more polyols, for example from about 2% to about 17% of one or more polyols, such as from about 2% to about 16% of one or more polyols, for example from about 2% to about 15% of one or more polyols.

5. The method according to any of the preceding items, wherein the paste prior to drying comprises between about 10% to about 60% of haemostatic agent, for example about 10% to about 50% of haemostatic agent, such as about 10% to about 40% of haemostatic agent, for example about 10% and about 30% of haemostatic agent, such as about 12% to about 25% of haemostatic agent, for example about 14% to about 25% of haemostatic agent, such as about 15% to about 25% of haemostatic agent, for example about 16% to about 20% of haemostatic agent, such as about 17% to about 20% of haemostatic agent, for example about 18% to about 20% of haemostatic agent.

6. The method according to any of the preceding items, wherein the paste prior to drying comprises between about 50% and about 90% of water, such as between about 55% and about 85% of water, for example between about 60% and about 80% of water.

7. The method according to any of the preceding items, wherein the paste prior to drying comprises:
    a. from about 2% to about 40% of one or more polyols,
    b. from about 10% to about 60% of haemostatic agent, and
    c. from about 50% and about 90% of water.

8. The method according to any of the preceding items, wherein the paste prior to drying comprises:
   a. from about 5% to about 20% of one or more polyols,
   b. from about 15% to about 25% of haemostatic agent, and
   c. from about 60% to about 80% of water.
9. The method according to any of the preceding items, wherein the paste prior to drying and the dry haemostatic composition comprises a polyol:hemostatic agent ratio between about 0.1:1 and 1:1; such as between about 0.3:1 and 1:1.
10. The method according to any of the preceding items, wherein the composition after drying comprises less than about 5% of water, preferably less than about 2% of water, more preferred less than about 1.5% of water, even more preferred less than about 1% of water.
11. The method according to any of the preceding items, wherein the one or more polyols is selected from sugar alcohols, sugars and/or derivatives thereof.
12. The method according to item 11, wherein the one or more sugar alcohols is selected from the group consisting of glycol, glycerol, erythritol, threitol, arabitol, xylitol, ribitol, mannitol, sorbitol, dulcitol, fucitol, iditol, inositol, volemitol, isomalt, maltitol, lactitol and polyglycitol.
13. The method according to item 12, wherein the one or more sugar alcohols comprise mannitol and/or glycerol.
14. The method according to any of the preceding items, wherein the dry haemostatic composition further comprises one or more bioactive agents that stimulate haemostasis or wound, bone and/or tendon healing.
15. The method according to item 14, wherein the bioactive agent is thrombin.
16. The method according to any of the preceding items, wherein the drying is freeze-drying.
17. The method according to any of the preceding items, wherein the paste is frozen before drying.
18. The method according to any of the preceding items, wherein the aqueous medium is selected from the group consisting of water, saline and a buffered aqueous medium.
19. The method of any of the preceding items, wherein the paste is dried within a container, such as one selected from the group consisting of a vial, a jar, a tube, a tray or a syringe.
20. The method according to any of the preceding items, wherein the method comprises a further step of placing the dry haemostatic composition into an outer packaging.
21. The method according to item 20, wherein the outer packaging comprises aluminium foil packaging.
22. The method according to any of the preceding items, wherein the method comprises a further step of sterilising the dry haemostatic composition.
23. The method according to any of the preceding items, wherein the dry haemostatic composition reconstitutes to form a haemostatic paste without mechanical mixing within less than about 30 seconds, preferably within less than about 20 seconds, more preferred within less than about 10 seconds, even more preferred within less than about 5 seconds.
24. A dry haemostatic composition comprising a haemostatic agent and one or more polyols.
25. The dry haemostatic composition according to item 24, wherein the haemostatic agent is gelatine.
26. The dry haemostatic composition according to any of items 24 to 25, wherein the haemostatic agent is cross-linked.
27. The dry haemostatic composition according to any of items 24 to 26, wherein the composition comprises from about 10% to about 60% of one or more polyols, such as from about 20% to about 50% of one or more polyols, for example from about 20% to about 50%, such as from about 20% to about 45% of one or more polyols.
28. The dry haemostatic composition according to any of items 24 to 27, wherein the composition comprises between about 40% and 80% of haemostatic agent, such as between about 45% and 80% of haemostatic agent, for example between about 50% and 80% of haemostatic agent.
29. The dry haemostatic composition according to any of items 24 to 28, wherein the composition comprises less than about 5% of water, preferably less than about 2% of water, more preferred less than about 1.5% of water, even more preferred less than about 1% of water.
30. The dry haemostatic composition according to any of items 24 to 29, wherein the composition comprises:
   a. from about 10% to about 60% of one or more polyols,
   b. from about 40% to about 80% of haemostatic agent, and
   c. from about 0.1% to about 5% of water.
31. The dry haemostatic composition according to any of items 24 to 30, wherein the composition comprises:
   a. from about 20% to about 50% of one or more polyols,
   b. from about 50% to about 80% of haemostatic agent, and
   c. from about 0.1% to about 2% of water.
32. The dry haemostatic composition according to any of items 24 to 31, wherein the composition further comprises one or more bioactive agents that stimulate haemostasis or wound, bone and/or tendon healing.
33. The dry haemostatic composition according to item 32, wherein the bioactive agent is thrombin.
34. The dry haemostatic composition according to any of items 24 to 33, wherein said dry haemostatic composition reconstitutes to form a haemostatic paste without mechanical mixing within less than about 30 seconds, preferably within less than about 20 seconds, more preferred within less than about 10 seconds, even more preferred within less than about 5 seconds.
35. A haemostatic paste prepared by a process comprising the addition of an aqueous medium to the dry haemostatic composition obtained by the method of any of items 1 to 23 or to the dry composition of any of items 24 to 34, wherein no mechanical mixing is required for preparing said paste.
36. Use of the haemostatic paste according to item 35 to promote haemostasis and/or wound, bone and/or tendon healing in an individual in need thereof.
37. A haemostatic kit comprising:
   a. the dry haemostatic composition obtained by the method of any of items 1 to 23 or the dry haemostatic composition according to any of items 24 to 34,
   b. a container,
   c. an aqueous medium, and
   d. optionally an outer packaging.

EXAMPLES

Example 1

Haemostatic Pastes Comprising Varying Amounts of Mannitol and Glycerol

Materials
50 g Gelatine powder (milled crosslinked gelatine sponges)
200 ml buffer
Polyols
50% Benzalkoniumchloride (BAC)
0.9% Saline solution x and y g Mannitol and Glycerol according to the following plan:

| Formulation [#] | X: Mannitol [g] | Y: Glycerol [g] |
|---|---|---|
| 1 | 20 | 3 |
| 2 | 5 | 3 |
| 3 | 12.5 | 5 |
| 4 | 12.5 | 5 |
| 5 | 20 | 5 |
| 6 | 5 | 7 |
| 7 | 5 | 5 |
| 8 | 20 | 7 |
| 9 | 12.5 | 3 |
| 10 | 12.5 | 7 |
| 11 | 0 | 0 |

Equipment
Freeze dryer: Leybold-Heraus, Lyovac GT2 or Christ Alpha 1-4 LSC
Mixer: Kenwood, Major KM616
Method
Buffer Solution:
Add 2.0 g±0.1 g BAC (50%) to a 250 mL blue cap bottle
Add 98.0 g±0.5 g saline solution to the BAC
Mix for 2 minutes using magnetic stirring—this is the BAC stock solution
Add 123.0 g±0.5 g glycerol to a 2000 mL measuring flask
Add 10 g±0.5 g BAC stock solution
Add saline to the 2000 mL mark
Place a stopper in the flask and turn it upside down a few times
Mix by magnetic stirring for 5±1 minutes
Paste:
Dissolve xg polyol(s) in 200 ml buffer solution under stirring in the mixer. Add 50 g gelatine powder and mix with the dissolved polyol(s) until a homogeneous paste is obtained, approximately 5 minutes. Mixing of the paste was performed at room temperature, approximately 20° C.
Freeze-Drying:
The resulting paste is filled into 10 ml single use plastic syringes (5.5 ml per syringe) and placed at −30° C. for minimum 4 h. The frozen paste is transferred to the freeze-dryer and freeze dried until dry for 15 h.
Reconstitution:
The dry composition is reconstituted by adding 8 ml of liquid to each syringe, i.e. the amount of water which was removed from the composition during the freeze drying process is added. No mechanical mixing or stirring was used. The water was simply added to the dry composition and the composition left untouched until a paste was re-formed.
Results
The different formulations were tested for time to reconstitution, i.e. the time needed for a paste suitable for haemostatic purposes to spontaneously form without mechanical agitation of any sorts.

| Formulation [#] | X: Mannitol [g] | Y: Glycerol [g] | Time to reconstitution [sec]* |
|---|---|---|---|
| 1 | 20 | 3 | 4 |
| 2 | 5 | 3 | 15 |
| 3 | 12.5 | 5 | 8 |
| 4 | 12.5 | 5 | 8.5 |
| 5 | 20 | 5 | 5 |
| 6 | 5 | 7 | 10 |
| 7 | 5 | 5 | 20 |
| 8 | 20 | 7 | 4 |
| 9 | 12.5 | 3 | 5 |
| 10 | 12.5 | 7 | 4 |
| 11 | 0 | 0 | 55 |

*Triplicate determination

Formulation 11 is a negative control. The consistency of the formulation 11 paste was clearly inferior to the consistency of the pastes containing mannitol and glycerol in varying amounts.

Formulation 5

Formulation 5 had a spontaneous reconstitution time of 5 seconds. The contents of formulation 5 are specified in the table below in the paste (wet) and the dried composition (dry) respectively.

| Formulation 5 | Content wet [g] | Content dry [g] | Content wet [%] | Content dry [%] |
|---|---|---|---|---|
| Gelatine | 50.00 | 50.00 | 18.18 | 56.65 |
| Mannitol | 20.00 | 20.00 | 7.27 | 22.66 |
| Glycerol (buffer) | 12.30 | 12.30 | 4.47 | 13.94 |
| Glycerol (added) | 5.00 | 5.00 | 1.82 | 5.67 |
| BAC | 0.01 | 0.01 | 0.00 | 0.01 |
| NaCl | 0.01 | 0.01 | 0.00 | 0.01 |
| $H_2O$ | 187.68 | 0.94 | 68.25 | 1.06 |
| SUM | 275.00 | 88.26 | 100 | 100 |

The total percentage of glycerol in formulation 5 in the paste was thus 6.29% and in the dried composition 19.61%.

The total polyol concentration, i.e. mannitol and glycerol, in the paste was 13.56% and after drying 42.27%.

The polyol:gelatine ratio in the dry composition was approximately 0.75:1.

Example 2

Mannitol and Glycerol

A paste was made, dried and reconstituted according to the method described in Example 1. The contents of the paste are shown in the table below.

| | Content wet [g] | Content dry [g] | Content wet [%] | Content dry [%] |
|---|---|---|---|---|
| Gelatine | 50.00 | 50.00 | 18.52 | 60.05 |
| Mannitol | 20.00 | 20.00 | 7.41 | 24.02 |
| Glycerol (buffer) | 12.30 | 12.30 | 4.56 | 14.77 |
| Glycerol (added) | 0 | 0 | 0 | 0 |
| BAC | 0.01 | 0.01 | 0.00 | 0.01 |
| NaCl | 0.01 | 0.01 | 0.00 | 0.01 |
| $H_2O$ | 187.68 | 0.94 | 69.51 | 1.13 |
| SUM | 270.00 | 83.26 | 100 | 100 |

The spontaneous reconstitution time of the paste made according to the table above was 6 seconds.

The total polyol concentration, i.e. mannitol and glycerol, in the paste was 11.97% and after drying 38.79%.

The polyol:gelatine ratio in the dry composition was approximately 0.65:1.

Example 3

Mannitol

A paste was made, dried and reconstituted according to the method described in Example 1 with the exception that water was used instead of the buffer solution of Example 1. The contents of the paste are shown in the table below.

|  | Content wet [g] | Content dry [g] | Content wet [%] | Content dry [%] |
|---|---|---|---|---|
| Gelatine | 50.00 | 50.00 | 18.52 | 70.42 |
| Mannitol | 20.00 | 20.00 | 7.41 | 28.17 |
| H$_2$0 | 200.00 | 1.00 | 74.07 | 1.41 |
| SUM | 270.00 | 71.00 | 100 | 100 |

The spontaneous reconstitution time of the paste made according to the table above was 7 seconds.

The results of the present example show that a paste of a suitable consistency for haemostatic purposes can be obtained from a freeze dried paste comprising only gelatine, water and a single polyol, in this case mannitol.

The polyol:gelatine ratio in the dry composition was approximately 0.4:1.

Example 4

Trehalose and Glycerol

A paste was made, dried and reconstituted according to the method described in Example 1. The contents of the paste are shown in the table below.

|  | Content wet [g] | Content dry [g] | Content wet [%] | Content dry [%] |
|---|---|---|---|---|
| Gelatine | 50.00 | 50.00 | 18.52 | 60.05 |
| Trehalose | 20.00 | 20.00 | 7.41 | 24.02 |
| Glycerol (buffer) | 12.30 | 12.30 | 4.56 | 14.77 |
| Glycerol (added) | 0 | 0 | 0 | 0 |
| BAC | 0.01 | 0.01 | 0.00 | 0.01 |
| NaCl | 0.01 | 0.01 | 0.00 | 0.01 |
| H$_2$0 | 187.68 | 0.94 | 69.51 | 1.13 |
| SUM | 270.00 | 83.26 | 100 | 100 |

The spontaneous reconstitution time of the paste made according to the table above was 8 seconds.

The total polyol concentration, i.e. trehalose and glycerol, in the paste was 11.97% and after drying 38.79%.

The polyol:gelatine ratio in the dry composition was approximately 0.65:1.

Example 5

Thrombin

Thrombin was included in the formulation 5 paste of Example 1 at a theoretical concentration of 2500 IU/product (8 ml). The paste was made at room temperature (approximately 20° C.) and mixed as described in Example 1.

The resulting paste was dried by freeze-drying and reconstituted as described in Example 1. The thrombin activity was measured in the reconstituted paste. The results are shown in the table below.

| Thrombin Activity - Freeze-dried composition in syringe [IU/product] | | |
|---|---|---|
| 2519.60 | 2884.94 | 2796.71 |

Mean activity: 2733.75

No loss of thrombin activity was measured in the reconstituted paste.

The results further show that it is not strictly necessary to perform the mixing of the paste at low temperatures to avoid loss of thrombin activity as no decrease in thrombin activity was found when mixing was performed at ambient temperatures.

Example 6

Different Polyols

Pastes comprising different polyols were made, dried and reconstituted essentially as described in Example 1 with the exception that H$_2$O with BAC was used instead of the buffer of example 1. The contents of the paste are shown in the tables below.

|  | Content wet [g] | Content dry [g] | Content wet [W/W %] | Content dry [W/W %] |
|---|---|---|---|---|
| Gelatine | 50.00 | 50.00 | 18.52 | 70.41 |
| Mannitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Xylitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Trehalose | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Maltitol | 20.00 | 20.00 | 7.41 | 28.17 |
| BAC | 0.01 | 0.01 | 0.00 | 0.01 |
| H$_2$0 | 200 | 1.00 | 74.07 | 1.41 |
| SUM | 270.01 | 71.01 | 100 | 100 |

|  | Content wet [g] | Content dry [g] | Content wet [%] | Content dry [%] |
|---|---|---|---|---|
| Gelatine | 50.00 | 50.00 | 18.52 | 70.41 |
| Sorbitol | 20.00 | 20.00 | 7.41 | 28.17 |
| BAC | 0.01 | 0.01 | 0.00 | 0.01 |
| H₂0 | 200 | 1.00 | 74.07 | 1.41 |
| SUM | 270.01 | 71.01 | 100 | 100 |

The polyol:gelatine ratio in the dry compositions was approximately 0.4:1.

Figure 2:
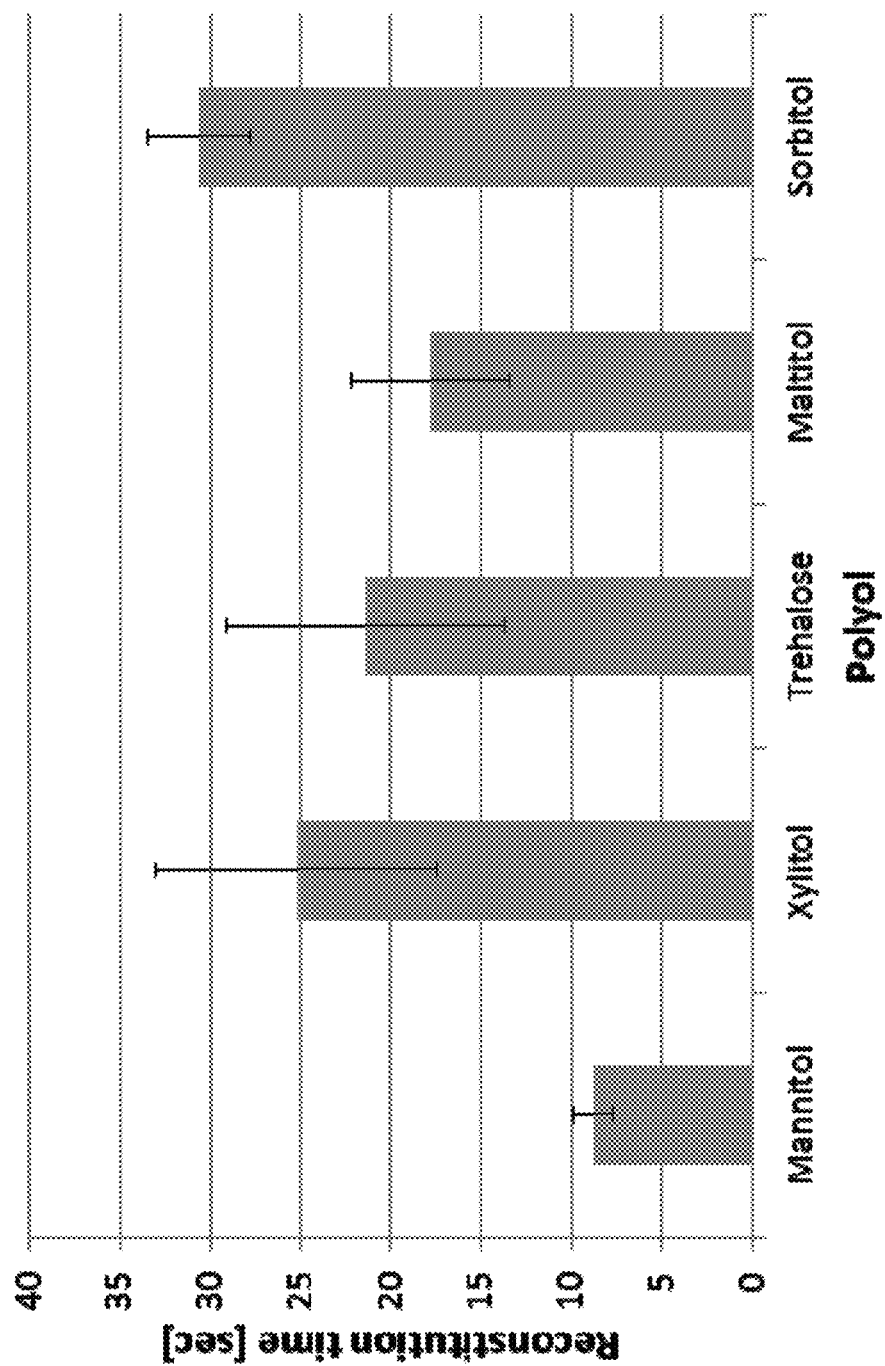
FIG. 2. Average reconstitution time+/−standard deviation of the freeze-dried gelatine pastes comprising different polyols of example 6.

The spontaneous reconstitution time of the pastes comprising different polyols made according to the tables above is shown in the table below and in FIG. 2. The experiments were repeated 5 times for each polyol.

Reconstitution time in seconds:

|  | Mannitol | Xylitol | Trehalose | Maltitol | Sorbitol |
|---|---|---|---|---|---|
| 1 | 7 | 14 | 11 | 14 | 29 |
| 2 | 9 | 31 | 28 | 14 | 28 |
| 3 | 9 | 20 | 16 | 23 | 29 |
| 4 | 10 | 30 | 29 | 16 | 35 |
| 5 | 9 | 31 | 23 | 22 | 32 |
| Average | 8.8 | 25.2 | 21.4 | 17.8 | 30.6 |
| Std | 1.1 | 7.8 | 7.8 | 4.4 | 2.9 |

The experiment shows that different kinds of polyols can be used for making a freeze-dried gelatine paste that will reconstitute spontaneously upon addition of water. The reconstituted paste has a consistency suitable for direct use as a haemostatic paste.

The invention claimed is:

1. A method of preparing a dry composition suitable for use in haemostasis and wound healing, comprising the sequential steps of:
    a) providing a cross-linked biocompatible polymer in powder form, one or more polyols and an aqueous medium, wherein the one or more polyols are selected from sugar alcohols and sugars;
    b) mixing the biocompatible polymer, the one or more polyols and the aqueous medium to obtain a paste; and
    c) freeze-drying the paste to produce a dry composition, wherein the dry composition is capable of reconstituting to form a substantially homogeneous paste without mechanical mixing, wherein the dry composition comprises from 10% w/w to 60% w/w of one or more polyols.

2. The method according to claim 1, wherein the paste prior to drying comprises from 3% w/w to 20% w/w of one or more polyols.

3. The method according to claim 1, wherein the biocompatible polymer is gelatine.

4. The method according to claim 3, wherein the gelatine is obtained from a cross-linked gelatine sponge.

5. The method according to claim 1, wherein the paste prior to freeze-drying comprises:
    a) from 5% w/w to 20% w/w of one or more polyols;
    b) from 15% w/w to 25% w/w of biocompatible polymer; and
    c) from 60% w/w to 80% w/w of water.

6. The method according to claim 1, wherein the dry composition comprises less than 5% w/w of water.

7. The method according to claim 1, wherein the one or more sugar alcohols is selected from glycol, glycerol, erythritol, threitol, arabitol, xylitol, ribitol, mannitol, sorbitol, dulcitol, fucitol, iditol, inositol, volemitol, isomalt, maltitol, lactitol or polyglycitol.

8. The method according to claim 1, wherein the one or more polyols is mannitol.

9. The method according to claim 8, where the dry composition comprises one or more further polyols.

10. The method according to claim 1, wherein the dry composition further comprises one or more bioactive agents that stimulate haemostasis or wound, bone, tendon and/or tissue healing.

11. The method according to claim 10, wherein the bioactive agent is thrombin.

12. The method according to claim 1, wherein the aqueous medium is selected from water, saline, a calcium chloride solution or a buffered aqueous medium.

13. The method according to claim 1, wherein the method comprises a further step of placing the dry composition into an outer packaging.

14. The method according to claim 13, wherein the outer packaging is an aluminium foil packaging.

15. The method according to claim 1, wherein the method comprises a further step of sterilising the dry composition.

16. The method according to claim 1, wherein the paste is filled into and freeze-dried within a syringe or applicator suitable for dispensing flowable haemostatic compositions.

17. The method according to claim 1, wherein the dry composition comprises from 20% w/w to 60% w/w of one or more polyols.

18. The method according to claim 1, wherein the dry composition comprises from 25% w/w to 60% w/w of one or more polyols.

19. A method for reconstituting a dry composition suitable for use in haemostasis and wound healing, comprising the sequential steps of:
    a) providing a cross-linked biocompatible polymer in powder form, one or more polyols and an aqueous medium, wherein the one or more polyols are selected from sugar alcohols and sugars;
    b) mixing the biocompatible polymer, the one or more polyols and the aqueous medium to obtain a paste;
    c) freeze-drying the paste to produce a dry composition, wherein the dry composition is capable of reconstituting to form a substantially homogeneous paste without mechanical mixing, wherein the dry composition comprises from 10% w/w to 60% w/w of one or more polyols; and
    d) adding an aqueous medium to the dry composition, thereby forming a paste without the need for mechanical mixing.

20. The method according to claim 19, wherein the dry composition is present in a container.

21. The method according to claim 20, wherein the container is a syringe.

* * * * *